US007135586B2

(12) United States Patent
Meerpoel et al.

(10) Patent No.: US 7,135,586 B2
(45) Date of Patent: Nov. 14, 2006

(54) BIPHENYLCARBOXAMIDES USEFUL AS LIPID LOWERING AGENTS

(75) Inventors: Lieven Meerpoel, Beerse (BE); Leo Jacobs Jozef Backx, Beerse (BE)

(73) Assignee: Janssen Pharmaceutica, NV (BE)

( * ) Notice: Subject to any disclaimer, the term of this patent is extended or adjusted under 35 U.S.C. 154(b) by 0 days.

(21) Appl. No.: 10/432,404

(22) PCT Filed: Nov. 15, 2001

(86) PCT No.: PCT/EP01/13316

§ 371 (c)(1),
(2), (4) Date: Dec. 24, 2003

(87) PCT Pub. No.: WO02/42271

PCT Pub. Date: May 30, 2002

(65) Prior Publication Data

US 2004/0102490 A1    May 27, 2004

(30) Foreign Application Priority Data

Nov. 21, 2000  (EP)  ................... 00204150

(51) Int. Cl.
C07C 229/00 (2006.01)
C07C 233/00 (2006.01)
A01N 37/12 (2006.01)
A01N 37/18 (2006.01)

(52) U.S. Cl. .................... 560/39; 560/36; 560/37; 514/534; 514/535; 514/616; 564/157

(58) Field of Classification Search ............. 560/39, 560/36, 37; 514/534, 535, 616; 564/157
See application file for complete search history.

(56) References Cited

U.S. PATENT DOCUMENTS

| 3,910,930 A | 10/1975 | Janssen et al. |
|---|---|---|
| 3,929,801 A | 12/1975 | Janssen et al |
| 4,231,938 A | 11/1980 | Monaghan et al. |
| 4,329,348 A | 5/1982 | Huebner |
| 4,346,227 A | 8/1982 | Terahara et al. |
| 4,444,784 A | 4/1984 | Hoffman et al. |
| 4,470,989 A | 9/1984 | Ezzell et al. |
| 4,647,576 A | 3/1987 | Hoefle et al. |
| 4,739,073 A | 4/1988 | Kathawala |
| 4,847,271 A | 7/1989 | Chabala et al. |
| 5,041,432 A | 8/1991 | Gaylor et al. |
| 5,064,856 A | 11/1991 | Garrity et al. |
| 5,120,729 A | 6/1992 | Chabala et al. |
| 5,137,901 A | 8/1992 | Junge et al. |
| 5,177,080 A | 1/1993 | Angerbauer et al. |
| 5,371,094 A | 12/1994 | Heine et al. |
| 5,492,918 A | 2/1996 | Wild et al. |
| 5,510,379 A | 4/1996 | Lee et al. |
| 5,512,548 A | 4/1996 | Kushwaha et al. |
| 5,541,199 A | 7/1996 | Mewshaw |
| 5,696,136 A | 12/1997 | Heine et al. |
| 5,760,246 A | 6/1998 | Biller et al. |
| 5,827,875 A | 10/1998 | Dickson, Jr. et al. |
| 5,919,795 A | 7/1999 | Chang et al. |
| 5,965,577 A | 10/1999 | Tino |
| 5,968,950 A | 10/1999 | Quallich et al. |
| 6,133,277 A | 10/2000 | Wigerinck et al. |
| 2004/0014971 A1 | 1/2004 | Meerpoel et al. |
| 2004/0019051 A1 | 1/2004 | Van Emelen et al. |

FOREIGN PATENT DOCUMENTS

| CA | 2091102 | 9/1993 |
|---|---|---|
| CA | 2091102 A1 | 9/1993 |
| EP | 0491226 B1 | 6/1992 |
| EP | 0 643 057 A1 | 3/1995 |
| EP | 0643057 A1 | 3/1995 |
| EP | 0645377 B1 | 3/1995 |
| EP | 0645378 B1 | 8/2000 |
| EP | 0567026 B1 | 3/2003 |
| WO | WO 93/17017 A1 | 9/1993 |
| WO | WO 95/05383 A1 | 2/1995 |
| WO | WO 96/10559 A1 | 4/1996 |
| WO | WO 96/26205 A1 | 8/1996 |
| WO | WO 96/26948 A1 | 9/1996 |
| WO | WO 96/40640 A1 | 12/1996 |
| WO | WO 98/23593 A1 | 6/1998 |
| WO | WO 98/27979 A1 | 7/1998 |
| WO | WO 99/29687 A1 | 6/1999 |
| WO | WO 99/66407 A1 | 12/1999 |

(Continued)

OTHER PUBLICATIONS

Wiloughby, C., Chapman, K., Solid Phase Synthesis of Aryl Amines, Tetrahedron Letters, 1996, pp. 7181-7184, vol. 37, No. 40.

(Continued)

Primary Examiner—J. Parsa

(57) ABSTRACT

Biphenylcarboxamide compounds of formula (I)

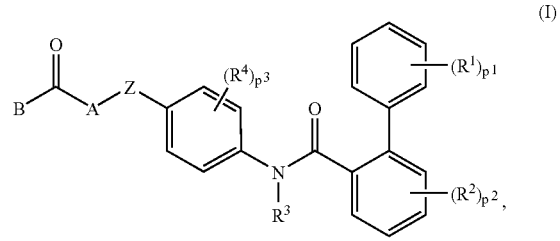

methods for preparing such compounds, pharmaceutical compositions comprising said compounds as well as the use of said compounds as a medicine for the treatment of hyperlipidemia, obesity and type II diabetes.

5 Claims, No Drawings

FOREIGN PATENT DOCUMENTS

| WO | WO 00/32582 A1 | 6/2000 |
|----|----|----|
| WO | WO 00/75136 A1 | 12/2000 |
| WO | WO 00/75137 A1 | 12/2000 |
| WO | WO 01/77077 A1 | 10/2001 |
| WO | WO 01/98306 A1 | 12/2001 |
| WO | WO 02/20501 A2 | 3/2002 |
| WO | WO 02/42271 A2 | 6/2002 |
| WO | WO 02/081460 A1 | 10/2002 |

OTHER PUBLICATIONS

Hudson, D., Methodological Implications of Simultaneous Solid-Phase Peptide Synthesis. 1. Comparison of Different Coupling Procedures, J. Org. Chem., 1988, pp. 617-624, vol. 53.

Pietzonka, T., Damon, R., Russell, M., Wattanasin, S., Phosphonate-Containing Analogs of Cholesteryl Ester as Novel Inhibitors of Cholesteryl Ester Transfer Protein, 1996, pp. 1951-1954, vol. 6, No. 16.

Chan, D., Monaco, K, Wang, R., Winters, M., New N-and O-Arylations with Phenylboronic Acids and Cupric Acetate, Tetrahedron Letters, 1998, pp. 2933-2936, vol. 39.

Wolfe, J., Wagaw, S, Buchwald, S., An Improved Catalyst System for Aromatic Carbon-Nitrogen Bond Formation: The Possible Involvement of Bis(phosphine) Palladium Complexes as Key Intermediates, J. Am. Chem. Soc. 1996, pp. 7215-7216, vol. 118.

Wetterau, J., Zilversmit, B. Purification and Characterization of Microsomal Triglyceride and Cholesteryl Ester Transfer Protein from Bovine Liver Microsomes, Chemistry and Physics of Lipids, vol. 38, 1985, pp. 205-222.

Sharp, D, Blinderman, L. Combs, K, Klenzie, B., Ricci, B. Wager-Smith,K, Gil, C., Turck C, Bouma, M., Rader, D, Aggerbeck, L., Gregg,R., Gordon, D, Wetterau, J., Cloning and gene defects in microsomal triglyceride transfer protein associated with a betalipoproteinaemia, Nature, vol. 365, 1993, pp. 65-69.

Kim, Y., Son, K. Name, J., Kim, S., Jeong, T. Lee, W. Bok, S. Kwon, B. Park, Y. Shin, J., Inhibition of Cholesteryl Ester Transfer Protein by Rosenonolactone Derivatives, The Journal of Antibiotics, vol. 49, No. 8, 1996, pp. 815-816.

Taylor, F. Kandutsch, A., Use of Oxygenated Stenols to Probe the Regulation of 3-Hydroxy-3-methylglutaryl-CoA Reductase and Sterologenesis, Methods in Enzymology, vol. 110, 1985, 9-19, Academic Press.

Miziorko, H., 3-Hydroxy-3-methylglutaryl-CoA Synthase from Chicken Liver, Methods in Enzymology, vol. 110, 1985, pp. 19-26, Academic Press.

Agnew, W., Squalene Synthetase, Methods in Enzymology, vol. 110, 1985, pp. 359-373, Academic Press.

Qureshi, N. , Nimmaniit, S., Porter, J., 3-Hydroxy-3-Methylglutaryl-CoA Reductase from Yeast, Methods in Enzymology, vol. 71, 1981, pp. 455-461, Academic Press.

Kleinsek, D., Dugan, R. Baker, D., Porter, J., 3-Hydroxy-3-Methylglutaryl-CoA Reductase from Rat Liver, Methods in Enzymology, vol. 71, 1981, pp. 462-479, Academic Press.

Rodwell, V., Bensch, W., S-3 Hydroxy-3Methylglutaryl-CoA Rductase from Pseudomonas, Methods in Enzymology, vol. 71, 1981, pp. 480-485, Academic Press.

Ingebritsen, T, Gibson, D., Assay of Enzymes that Modulate S-3-Hydroxy-3Methylglutaryl-CoA Reductase by Reversible Phosphorylation, Methods in Enzymology, vol. 71, 1981, pp. 486-509, Academic Press.

Mercer, E., Inhibitors of Sterol Biosynthesis and their Applications, Prog. Lipid Res., vol. 32, No. 4, 1993, pp. 357-416, Great Britain.

PCT Search Report dated Jul. 23, 2002 for International Application No. PCT/EP01/13316.

Sharpe, D. et al., "Cloning and gene defects in microsomal triglyceride transfer protein associated with abetalipoproteinaemia." Nature, 1993, pp. 65-69, vol. 365.

Akrakawa, T. "New Aspects of Gastric Adaptive Relaxation, Reflex after Food Intake for More Food: Involvement of Capsaicin-sensitive Sensory Nerves and Nitric Oxide." J. Smooth Muscle Res., 1997, pp. 81-88, vol. 33.

Wetterau, J. R. et al., "An MTP Inhibitor That Normalizes Atheroganic Lipoprotein Levels in WHHL Rabbits." Science, 1998, pp. 751-754., vol 282.

PCT International Search Report dated Aug. 1, 2002 for PCT Application No. PCT/EP01/13316 which relates to U.S. Appl. No. 10/432,404.

BIPHENYLCARBOXAMIDES USEFUL AS LIPID LOWERING AGENTS

CROSS REFERENCE TO RELATED APPLICATIONS

This application is the national stage of Application No. PCT/EP01/13316, filed Nov. 15, 2001 which claims priority from EP 00204150.7, filed Nov. 21, 2000.

The present invention is concerned with novel biphenylcarboxamide compounds having apolipoprotein B inhibiting activity and concomitant lipid lowering activity. The invention further relates to methods for preparing such compounds, pharmaceutical compositions comprising said compounds as well as the use of said compounds as a medicine for the treatment of hyperlipidemia, obesity and type II diabetes.

Obesity is the cause of a myriad of serious health problems like the adult onset of diabetes and heart disease. In addition, the loss of weight is getting an obsession among an increasing proportion of the human population.

The causal relationship between hypercholesterolemia, particularly that associated with increased plasma concentrations of low density lipoproteins (hereinafter referred as LDL) and very low density lipoproteins (hereinafter referred as VLDL), and premature atherosclerosis and/or cardiovascular disease is now widely recognized. However, a limited number of drugs are presently available for the treatment of hyperlipidemia. Drugs primarily used for the management of hyperlipidemia include bile acid sequestrant resins such as cholestyramine and colestipol, fibric acid derivatives such as bezafibrate, clofibrate, fenofibrate, ciprofibrate and gemfibrozil, nicotinic acid and cholesterol synthesis-inhibitors such as HMG Co-enzyme-A reductase inhibitors. The inconvenience of administration (a granular form to be dispersed in water or orange juice) and the major side-effects (gastrointestinal discomfort and constipation) of bile acid sequestrant resins constitute major drawbacks. Fibric acid derivatives induce a moderate decrease (by 5 to 25%) of LDL cholesterol (except in hypertriglyceridemic patients in whom initially low levels tend to increase) and, although usually well tolerated, suffer from side-effects including potentiation of warfarine, pruritus, fatigue, headache, insomnia, painful reversible myopathy and stiffness in large muscle groups, impotency and impaired renal function. Nicotinic acid is a potent lipid lowering agent resulting in a 15 to 40% decrease in LDL cholesterol (and even 45 to 60% when combined with a bile acid sequestrant resin) but with a high incidence of troublesome side-effects related to the drug's associated vasodilatory action, such as headache, flushing, palpitations, tachychardia and occasional syncopes, as well as other side-effects such as gastro-intestinal discomfort, hyperucemia and impairment of glucose tolerance. Among the family of HMG Co-enzyme-A reductase inhibitors, lovastatin and simvastatin are both inactive prodrugs containing a lactone ring which is hydrolyzed in the liver to form the corresponding active hydroxy-acid derivative. Inducing a reduction of LDL cholesterol by 35 to 45%, they are generally well tolerated with a low incidence of minor side effects. However there still remains a need for new lipid lowering agents with improved efficiency and/or acting via other mechanisms than the above mentioned drugs.

Plasma lipoproteins are water-soluble complexes of high molecular weight formed from lipids (cholesterol, triglyceride, phospholipids) and apolipoproteins. Five major classes of lipoproteins that differ in the proportion of lipids and the type of apolipoprotein, all having their origin in the liver and/or the intestine, have been defined according to their density (as measured by ultracentrifugation). They include LDL, VLDL, intermediate density lipoproteins (hereinafter referred as IDL), high density lipoproteins (hereinafter referred as HDL) and chylomicrons. Ten major human plasma apolipoproteins have been identified. VLDL, which is secreted by the liver and contains apolipoprotein B (hereinafter referred as Apo-B), undergoes degradation to LDL which transports 60 to 70% of the total serum cholesterol. Apo-B is also the main protein component of LDL. Increased LDL-cholesterol in serum, due to oversynthesis or decreased metabolism, is causally related to atherosclerosis. In contrast high density lipoproteins (hereinafter referred as HDL), which contain apolipoprotein A1, have a protective effect and are inversely correlated with the risk of a coronary heart disease. The HDL/LDL ratio is thus a convenient method of assessing the atherogenic potential of an individual's plasma lipid profile.

The two isoforms of apolipoprotein (apo) B, apo B-48 and apo B-100, are important proteins in human lipoprotein metabolism. Apo B-48, so named because it appears to be about 48% the size of apo B-100 on sodium dodecyl sulfate-polyacrylamide gels, is synthesized by the intestine in humans. Apo B-48 is necessary for the assembly of chylomicrons and therefore has an obligatory role in the intestinal absorption of dietary fats. Apo B-100, which is produced in the liver in humans, is required for the synthesis and secretion of VLDL. LDL, which contain about ⅔ of the cholesterol in human plasma, are metabolic products of VLDL. Apo B-100 is virtually the only protein component of LDL. Elevated concentrations of apo B-100 and LDL cholesterol in plasma are recognized risk factors for developing atherosclerotic coronary artery disease.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias have also been classified into common hypercholesterolaemia, familial combined hyperlipidaemia, familial hypercholesterolaemia, remnant hyperlipidaemia, chylomicronaemia syndrome and familial hyper-triglyceridaemia.

Microsomal triglyceride transfer protein (hereinafter referred as MTP) is known to catalyze the transport of triglyceride and cholesteryl ester by preference to phospholipids such as phosphatidylcholine. It was demonstrated by D. Sharp et al., *Nature* (1993) 365:65 that the defect causing abetalipoproteinemia is in the MTP gene. This indicates that MTP is required for the synthesis of Apo B-containing lipoproteins such as VLDL, the precursor to LDL. It therefore follows that an MTP inhibitor would inhibit the synthesis of VLDL and LDL, thereby lowering levels of VLDL, LDL, cholesterol and triglyceride in humans. MTP inhibitors have been reported in Canadian patent application No. 2,091,102 and in WO 96/26205. MTP inhibitors belonging to the class of polyarylcarboxamides have also been reported in U.S. Pat. No. 5,760,246 as well as in WO-96/40640 and WO-98/27979. U.S. Pat. No. 5,968,950 discloses 4'-trifluoro-methylbiphenyl-2-carboxylic acid-[2-(2-acetylamino-ethyl)-1,2,3,4-tetrahydro-isoquinolin-6-yl]-amide hydrochloride as an Apo B secretion/MTP inhibitor. U.S. Pat. No. 5,827,875 discloses pyrrolidinyl-substituted fluorenes as inhibitors of microsomal triglyceride transfer protein. U.S.

Pat. No. 5,965,577 discloses heterocyclic inhibitors of microsomal triglyceride transfer protein.

One of the goals of the present invention is to provide an improved treatment for patients suffering from obesity or atherosclerosis, especially coronary atherosclerosis and more generally from disorders which are related to atherosclerosis, such as ischaemic heart disease, peripheral vascular disease and cerebral vascular disease. Another goal of the present invention is to cause regression of atherosclerosis and inhibit its clinical consequences, particularly morbidity and mortality.

The present invention is based on the unexpected discovery that a class of novel biphenylcarboxamide compounds is acting as selective MTP inhibitors, i.e. is able to selectively block MTP at the level of the gut wall in mammals, and is therefore a promising candidate as a medicine, namely for the treatment of hyperlipidemia. The present invention additionally provides several methods for preparing such biphenylcarboxamide compounds, as well as pharmaceutical compositions including such compounds. Furthermore, the invention provides a certain number of novel compounds which are useful intermediates for the preparation of the therapeutically active biphenylcarboxamide compounds, as well as methods for preparing such intermediates. Finally, the invention provides a method of treatment of a condition selected from atherosclerosis, pancreatitis, obesity, hypercholesterolemia, hypertriglyceridemia, hyperlipidemia, diabetes and type II diabetes, comprising administering a therapeutically active biphenylcarboxamide compound to a mammal.

The present invention relates to a family of novel biphenylcarboxamide compounds of formula (I)

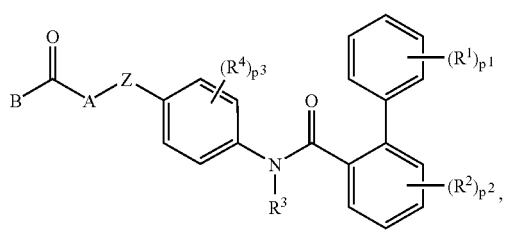

(I)

the N-oxides, the pharmaceutically acceptable acid addition salts and the stereochemically isomeric forms thereof, wherein $p^1$, $p^2$ and $p^3$ are integers each independently from 1 to 3;

each $R^1$ is independently selected from hydrogen, $C_{1-4}$alkyl, $C_{1-4}$alkyloxy, halo, hydroxy, mercapto, cyano, nitro, $C_{1-4}$alkylthio or polyhalo$C_{1-6}$alkyl, amino, $C_{1-4}$alkylamino and di($C_{1-4}$alkyl)amino;

each $R^2$ is independently selected from hydrogen, $C_{1-4}$alkyl, $C_{1-4}$alkyloxy, halo, or trifluoromethyl;

$R^3$ is hydrogen of $C_{1-4}$alkyl;

each $R^4$ is independently selected from hydrogen $C_{1-4}$alkyl, $C_{1-4}$alkyloxy, halo, or trifluoromethyl;

Z is a bivalent radical of formula

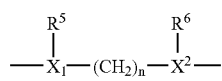

(a-1)

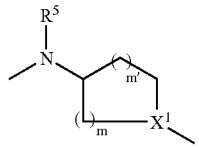

(a-2)

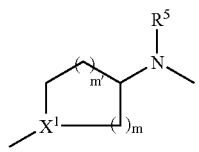

(a-3)

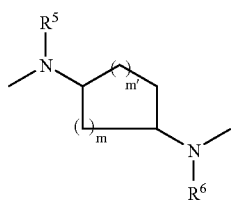

(a-4)

wherein n is an integer from 2 to 4 and the —$(CH_2)_n$— moiety in radical (a-1) may optionally be substituted with one or two $C_{1-4}$alkyl;

m and m' are integers from 1 to 3;

$R^5$ and $R^6$ are each independently selected from hydrogen, $C_{1-6}$alkyl or aryl;

$X^1$ and $X^2$ are each independently selected from CH, N or an $sp^2$ hybridized carbon atom and in radical (a-1) at least one of $X^1$ or $X^2$ is N;

A represents a bond, $C_{1-6}$alkanediyl optionally substituted with one or two groups selected from aryl, heteroaryl and $C_{3-10}$cycloalkyl;

B represents hydrogen; $C_{1-10}$alkyl; aryl or heteroaryl each optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkoxycarbonyl, $C_{1-10}$alkylaminocarbonyl and di($C_{1-10}$alkyl)aminocarbonyl; aryl$C_{1-10}$alkyl; heteroaryl$C_{1-10}$alkyl; $C_{3-10}$cycloalkyl; polyhalo$C_{1-6}$alkyl; $C_{3-8}$alkenyl; $C_{3-6}$alkynyl; $NR^7R^8$; or $OR^9$;

wherein $R^7$ and $R^8$ each independently represent hydrogen, $C_{1-10}$alkyl, aryl or heteroaryl each optionally substituted with a group selected from halo, cyano, $C_{1-4}$alkyloxy, amino, $C_{1-10}$alkylamino, di($C_{1-10}$alkyl) amino, $C_{1-10}$acyl, $C_{1-10}$alkylthio, $C_{1-10}$alkylaminocarbonyl and di($C_{1-10}$alkyl)aminocarbonyl; aryl$C_{1-10}$ alkyl, heteroaryl$C_{1-10}$alkyl, $C_{3-10}$cycloalkyl, $C_{7-10}$polycycloalkyl, polyhalo$C_{1-6}$alkyl, $C_{3-8}$alkenyl, $C_{3-8}$alkynyl, fused benzo-$C_{5-8}$cycloalkyl, and wherein $R^7$ and $R^8$ taken together with the nitrogen atom to which they are attached may form a saturated heterocyclic radical having from 4 to 8 carbon atoms; and wherein $R^9$ represents $C_{1-10}$alkyl, aryl or heteroaryl each optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkylaminocarbonyl and di($C_{1-10}$alkyl)aminocarbonyl; aryl$C_{1-10}$alkyl; heteroaryl$C_{1-10}$alkyl; $C_{3-10}$cycloalkyl; $C_{7-10}$polycycloalkyl; polyhalo$C_{1-6}$alkyl; $C_{3-8}$alkenyl; $C_{3-8}$alkynyl; or fused benzo$C_{5-8}$cycloalkyl.

Unless otherwise stated, as used in the foregoing definitions and hereinafter:

halo is generic to fluoro, chloro, bromo and iodo;

$C_{1-4}$alkyl defines straight and branched chain saturated hydrocarbon radicals having from 1 to 4 carbon atoms such as, for example, methyl, ethyl, propyl, n-butyl, 1-methylethyl, 2-methylpropyl, 1,1-dimethylethyl and the like;

$C_{1-6}$alkyl is meant to include $C_{1-4}$alkyl (as hereinabove defined) and the higher homologues thereof having 5 or 6 carbon atoms, such as for instance 2-methyl-butyl, n-pentyl, dimethylpropyl, n-hexyl, 2-methylpentyl, 3-methylpentyl and the like;

$C_{1-10}$alkyl is meant to include $C_{1-6}$alkyl (as hereinabove defined) and the higher homologues thereof having 7 to 10 carbon atoms, such as for instance heptyl, ethylhexyl, octyl, nonyl, decyl and the like;

$C_{3-10}$cycloalkyl is generic to cyclopropyl, cyclobutyl, cyclopentyl, cyclohexyl, cycloheptyl, cyclooctyl, cyclononyl and cyclodecyl;

polyhalo$C_{1-6}$alkyl is defined as polyhalosubstituted $C_{1-6}$alkyl, in particular $C_{1-6}$alkyl (as hereinabove defined) substituted with 2 to 13 halogen atoms such as difluoromethyl, trifluoromethyl, trifluoroethyl, octafluoropentyl and the like;

aryl is defined as mono- and polyaromatic groups such as phenyl optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkoxycarbonyl, $C_{1-10}$alkylaminocarbonyl and di($C_{1-10}$alkyl)aminocarbonyl;

heteroaryl is defined as mono- and polyheteroaromatic groups such as those including one or more heteroatoms selected from nitrogen, oxygen, sulfur and phosphorus, in particular pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl, thienyl and the like, including all possible isomeric forms thereof, and optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkoxycarbonyl, $C_{1-10}$alkylaminocarbonyl and di($C_{1-10}$alkyl)aminocarbonyl;

$C_{3-6}$alkenyl defines straight and branched chain hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl, 3-hexenyl, 2-hexenyl and the like;

$C_{3-6}$alkynyl defines straight and branched chain hydrocarbon radicals containing one triple bond and having from 3 to 6 carbon atoms such as, for example, 2-propynyl, 3-butynyl, 2-butynyl, 2-pentynyl, 3-pentynyl, 3-methyl-2-butynyl, 3-hexynyl, 2-hexynyl and the like;

$C_{4-8}$cycloalkenyl defines cyclic hydrocarbon radicals containing one double bond and having from 4 to 8 carbon atoms such as, for example cyclobutenyl, cyclopentenyl, cyclohexenyl, cycloheptenyl, cyclooctenyl and the like;

fused benzo$C_{5-8}$cycloalkyl defines radicals such as, for instance, indanyl, 1,2,3,4-tetrahydronaphtalenyl, fluorenyl and the like;

$C_{7-10}$polycycloalkyl defines radicals having from 7 to 10 carbon atoms such as, for instance, norbornyl;

$C_{1-6}$alkylamino defines primary amino radicals having from 1 to 6 carbon atoms such as, for example, methylamino, ethylamino, propylamino, isopropylamino, butylamino, isobutylamino and the like;

di($C_{1-6}$alkyl)amino defines secondary amino radicals having from 1 to 6 carbon atoms such as, for example, dimethylamino, diethylamino, dipropylamino, diisopropylamino, N-methyl-N'-ethylamino, N-ethyl-N'-propylamino and the like;

$C_{1-6}$alkylthio defines a $C_{1-6}$alkyl group attached to a sulfur atom, such as methylthio, ethylthio, propylthio, isopropylthio, butylthio and the like;

$C_{1-6}$acyl defines a $C_{1-6}$alkyl group attached to a carbonyl group such as, for instance acetyl, propionyl, butyryl, isobutyryl and the like.

Examples of the bivalent radical Z wherein one of $X^1$ or $X^2$ represents an $sp^2$ hybridized carbon atom are:

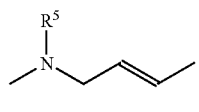 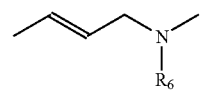

The pharmaceutically acceptable acid addition salts as mentioned hereinabove are meant to comprise the therapeutically active non-toxic acid addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I), which may be prepared in art-known manners, are meant to comprise those compounds of formula (I) wherein a nitrogen atom is oxidized to the N-oxide.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Unless otherwise mentioned or indicated, the chemical designation of compounds denotes the mixture of all possible stereoisomeric forms, said mixtures containing all diastereomers and enantiomers of the basic molecular structure. The same applies to the intermediates as described herein, used to prepare end products of formula (I).

The terms cis and trans are used herein in accordance with Chemical Abstracts nomenclature and refer to the position of the substituents on a ring moiety.

The absolute stereochemical configuration of the biphenylcarboxamide compounds of formula (I) and of the intermediates used in their preparation may easily be determined by those skilled in the art while using well-known methods such as, for example, X-ray diffraction.

Furthermore, some biphenylcarboxamide compounds of formula (I) and some of the intermediates used in their preparation may exhibit polymorphism. It is to be understood that the present invention encompasses any polymorphic forms possessing properties useful in the treatment of the conditions noted hereinabove.

A group of interesting compounds consists of those compounds of formula (I) wherein one or more of the following restrictions apply:
a) $R^1$ is hydrogen or trifluoromethyl;
b) $R^2$ is hydrogen;
c) $R^3$ is hydrogen;
d) $R^4$ is hydrogen;
e) $p^1$ is 1;
f) $p^2$ is 1;
g) $p^3$ is 1;
h) Z is a bivalent radical of formula (a-1) wherein $X^1$ and $X^2$ are each nitrogen;
i) Z is a bivalent radical of formula (a-2) wherein $X^1$ is nitrogen and m and m' are the integer 1;
j) Z is a bivalent radical of formula (a-2) wherein $X^1$ is nitrogen, m is the integer 2 and m' is the integer 1;
k) Z is a bivalent radical of formula (a-3) wherein $X^1$ is nitrogen and m and m' are the integer 1;
l) Z is a bivalent radical of formula (a-3) wherein $X^1$ is nitrogen, m is the integer 2 and m' is the integer 1;
m) Z is the bivalent radical of formula (a-4) wherein m is the integer 2 and m' is the integer 1;
n) $R^5$ and $R^6$ are each independently hydrogen or methyl;
o) the bivalent radical A is $C_{1-6}$alkanediyl substituted with one aryl group, in particular A is a methylene group substituted with phenyl;
p) B is $C_{1-4}$alkyloxy, or $C_{1-10}$alkylamino.

More interesting compounds are those compounds of formula (I) wherein $R^1$ is hydrogen or trifluoromethyl; $R^2$, $R^3$ and $R^4$ are hydrogen; and Z is a bivalent radical of formula (a-1) wherein $X^1$ and $X^2$ are each nitrogen, n is the integer 2, and $R^5$ and $R^6$ are each independently hydrogen or methyl.

Other more interesting compounds are those compounds of formula (I) wherein $R^1$ is hydrogen or trifluoromethyl; $R^2$, $R^3$ and $R^4$ are hydrogen; and Z is a bivalent radical of formula (a-2) or (a-3) wherein $X^1$ is nitrogen, m and m' are the integer 1, and $R^5$ and $R^6$ are each independently hydrogen or methyl.

Still other more interesting compounds are those compounds of formula (I) wherein $R^1$ is hydrogen or trifluoromethyl; $R^2$, $R^3$ and $R^4$ are hydrogen; and Z is a bivalent radical of formula (a-2) or (a-3) wherein $X^1$ is nitrogen, m is the integer 2, m' is the integer 1, and $R^5$ and $R^6$ are each independently hydrogen or methyl.

Yet other more interesting compounds are those compounds of formula (I) wherein $R^1$ is hydrogen or trifluoromethyl; $R^2$, $R^3$ and $R^4$ are hydrogen; and Z is a bivalent radical of formula (a-4) wherein m is the integer 2 and m' is the integer 1, and $R^5$ and $R^6$ are each independently hydrogen or methyl.

One advantage of the present invention is the easiness with which the compounds of formula (I) can be manufactured by a high number of different processes. Some of these processes will now be described in details, without pretending to provide an exhaustive list of the methods for preparing the said compounds.

A first process for preparing a biphenylcarboxamide compound according to this invention is a process wherein an intermediate phenylene amine having the formula

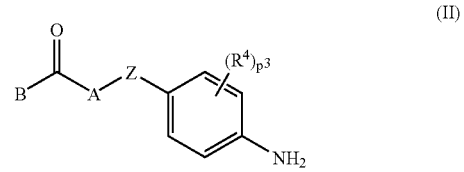

wherein B, A, Z and $R^4$ are as defined in formula (I), is reacted with a biphenyl-carboxylic acid or halide having the formula (III),

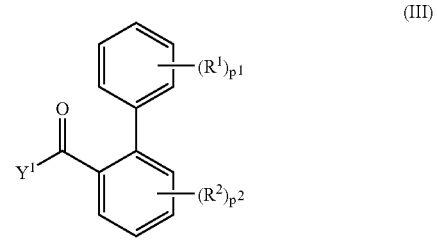

wherein $R^1$ and $R^2$ are as defined in formula (I) and $Y^1$ is selected from hydroxy and halo, in at least one reaction-inert solvent and optionally in the presence of a suitable base, the said process further optionally comprising converting a compound of formula (I) into an addition salt thereof, and/or preparing stereochemically isomeric forms thereof. In case $Y^1$ is hydroxy, it may be convenient to activate the biphenylcarboxylic acid of formula (III) by adding an effective amount of a reaction promoter. Non-limiting examples of such reaction promoters include carbonyldiimidazole, diimides such as N,N'-dicyclohexylcarbodiimide or 1-(3-dimethylaminopropyl)-3-ethylcarbodiimide, and functional derivatives thereof. For this type of acylation procedure, it is preferred to use a polar aprotic solvent such as, for instance, methylene chloride. Suitable bases for carrying out this first process include tertiary amines such as triethylamine, triisopropylamine and the like. Suitable temperatures for carrying out the first process of the invention typically range from about 20° C. to about 140° C., depending on the particular solvent used, and will most often be the boiling temperature of the said solvent.

A second process for preparing a biphenylcarboxamide compound of the invention is a process wherein an intermediate having the formula (IV)

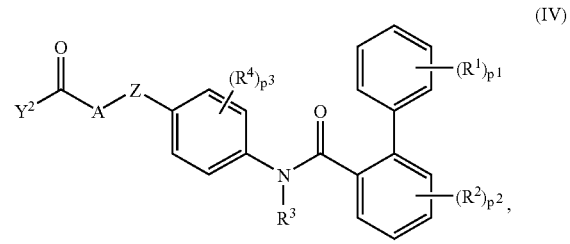

wherein $R^1$, $R^2$, $R^3$, $R^4$, A and Z are as defined in formula (I) and $Y^2$ is selected from halo and hydroxy, is reacted with an intermediate (V) of the formula B-H, wherein B is $NR^7R^8$ or $OR^9$ and $R^7$, $R^8$ and $R^9$ are as defined in formula (I), in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof. In case $Y^2$ is hydroxy, it may be convenient to activate the carboxylic acid of formula (IV) by adding an effective amount of a reaction promoter. Non-limiting examples of such reaction promoters include carbonyldiimidazole, diimides such as N,N'-dicyclohexylcarbodiimide or 1-(3-dimethylaminopropyl)-3-ethylcarbo-diimide, and functional derivatives thereof. In case a chirally pure reactant of formula (V) is used, a fast and enantiomerization-free reaction of the intermediate of formula (IV) with the said intermediate (V) may be performed in the further presence of an effective amount of a compound such as hydroxybenzotriazole, benzotriazolyloxytris (dimethylamino)phosphonium hexafluorophosphate, tetrapyrrolidinophosphonium hexafluorophosphate, bromotripyrrolidinophosphonium hexafluorophosphate, or a functional derivative thereof, such as disclosed by D. Hudson, *J. Org. Chem.* (1988), 53:617. In case $Y^2$ is hydroxy and B is $OR^9$, then the esterification reaction may conveniently be performed in the presence of an effective amount of an acid such as sulfuric acid and the like.

A third process for preparing a biphenylcarboxamide compound according to this invention is a process wherein an intermediate having the formula (VI)

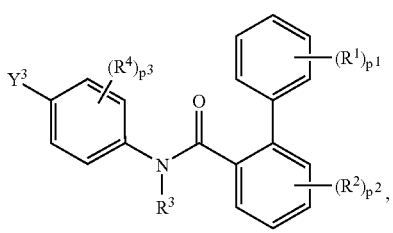

(VI)

wherein $R^1$, $R^2$, $R^3$, and $R^4$ are as defined in formula (I) and $Y^3$ is selected from halo, $B(OH)_2$, alkylboronates and cyclic analogues thereof, is reacted with a reactant having the formula (VII)

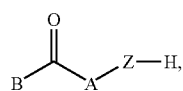

(VII)

wherein B, A and Z are as defined in formula (I), in at least one reaction-inert solvent and optionally in the presence of at least one transition metal coupling reagent and/or at least one suitable ligand, the said process further optionally comprising converting a compound of formula (I) into an addition salt thereof, and/or preparing stereochemically isomeric forms thereof. This type of reaction being known in the art as the Buchwaldt reaction, reference to the applicable metal coupling reagents and/or suitable ligands, e.g. palladium compounds such as palladium tetra(triphenyl-phosphine), tris(dibenzylidene-acetone dipalladium, 2,2'-bis (diphenylphosphino)-1,1'-binaphtyl and the like, may be found for instance in *Tetrahedron Letters* (1996) 37(40) 7181–7184 and *J. Am. Chem. Soc.* (1996) 118:7216. If $Y^3$ is $B(OH)_2$, an alkylboronate or a cyclic analogue thereof, then cupric acetate should be used as the coupling reagent, according to *Tetrahedron Letters* (1998) 39:2933–6.

The compounds of formula (I) can conveniently be prepared using solid phase synthesis techniques as depicted in Scheme 1 below. In general, solid phase synthesis involves reacting an intermediate in a synthesis with a polymer support. This polymer supported intermediate can then be carried on through a number of synthetic steps. After each step, impurities are removed by filtering the resin and washing it numerous times with various solvents. At each step the resin can be split up to react with various intermediates in the next step thus allowing for the synthesis of a large number of compounds. After the last step in the procedure the resin is treated with a reagent or process to cleave the resin from the sample. More detailed explanation of the techniques used in solid phase chemistry are described in for example "The Combinatorial Index" (B. Bunin, Academic Press) and Novabiochem's 1999 Catalogue & Peptide Synthesis Handbook (Novabiochem A G, Switzerland) both incorporated herein by reference.

Scheme 1:

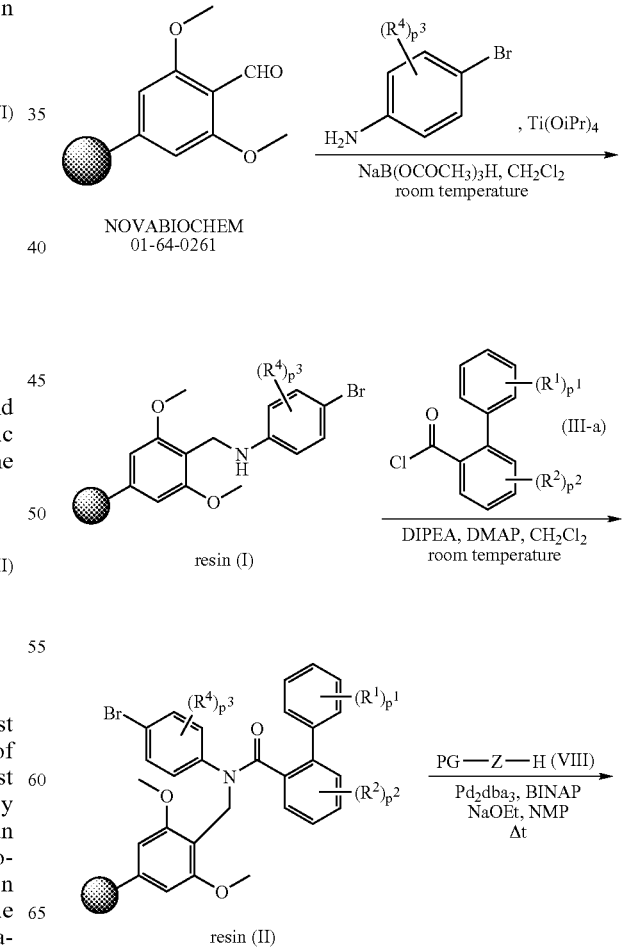

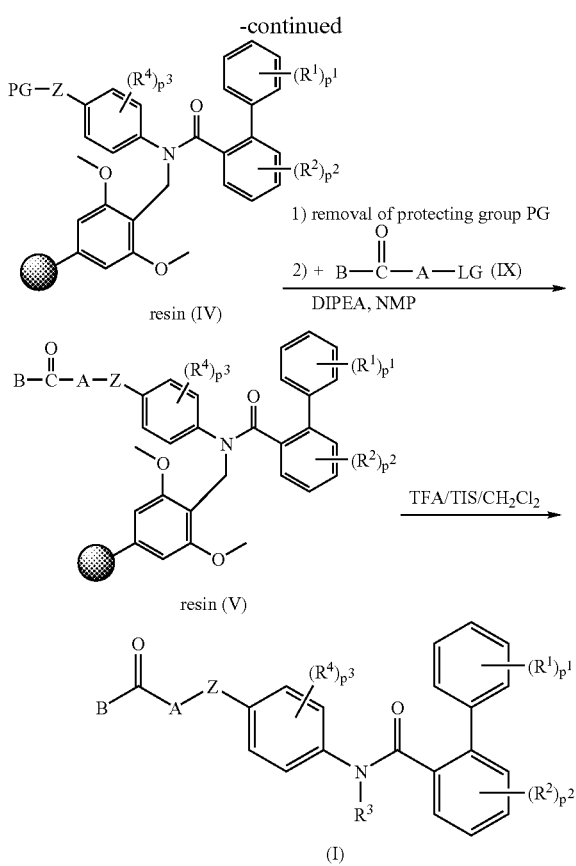

The abreviations used in Scheme 1 are explained in the Experimental Part. The substituents $R^1$, $R^2$, $R^3$, $R^4$, A, B, and Z are as defined for compounds of formula (I). PG represents a protecting group such as, e.g. t-butoxycarbonyl, $C_{1-6}$alkyloxycarbonyl, phenylmethyloxycarbonyl and the like.

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The biphenylcarboxamide compounds of formula (I), the N-oxide forms, the pharmaceutically acceptable salts and stereoisomeric forms thereof possess favourable apolipoprotein B inhibiting activity and concomitant lipid lowering activity. Therefore the present compounds are useful as a medicine especially in a method of treating patients suffering from hyperlipidemia, obesity, atherosclerosis or type II diabetes. In particular the present compounds may be used for the manufacture of a medicine for treating disorders caused by an excess of very low density lipoproteins (VLDL) or low density lipoproteins (LDL), and especially disorders caused by the cholesterol associated with said VLDL and LDL.

The causal relationship between hypercholesterolemia—particularly that associated with increased plasma concentrations of low density lipoproteins (LDL) and very low density lipoproteins (VLDL)—and premature atherosclerosis and cardiovascular disease is well established. VLDL is secreted by the liver and contains apolipoprotein B (apo-B); these particles undergo degradation in the circulation to LDL, which transports about 60 to 70% of the total serum cholesterol. Apo-B is also the principal protein component of LDL. Increased LDL-cholesterol in serum, due to oversynthesis or decreased metabolism, is causally related to atherosclerosis. In contrast, high density lipoproteins (HDL) which contain apolipoprotein A1, have a protective effect and are inversely correlated with risk of coronary heart disease. The HDL/LDL ratio is thus a convenient method of assessing the atherogenic potential of an individual's plasma lipid profile.

The principal mechanism of action of the compounds of formula (I) appears to involve inhibition of MTP (microsomal triglyceride transfer protein) activity in hepatocytes and intestinal epithelial cells, resulting in decreased VLDL and chylomicron production, respectively. This is a novel and innovative approach to hyperlipidemia, and is expected to lower LDL-cholesterol and triglycerides through reduced hepatic production of VLDL and intestinal production of chylomicrons.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias are common hypercholesterolaemia, familial combined hyperlipidaemia, familial hypercholesterolaemia, remnant hyperlipidaemia, chylomicronaemia syndrome, familial hypertriglyceridaemia. The present compounds may also be used to prevent or treat patients suffering from obesitas or from atherosclerosis, especially coronary atherosclerosis and more in general disorders which are related to atherosclerosis, such as ischaemic heart disease, peripheral vascular disease, cerebral vascular disease. The present compounds may cause regression of atherosclerosis and inhibit the clinical consequences of atherosclerosis, particularly morbidity and mortality.

In view of the utility of the compounds of formula (I), it follows that the present invention also provides a method of treating warm-blooded animals, including humans, (generally called herein patients) suffering from disorders caused by an excess of very low density lipoproteins (VLDL) or low density lipoproteins (LDL), and especially disorders caused by the cholesterol associated with said VLDL and LDL. Consequently a method of treatment is provided for relieving patients suffering from conditions, such as, for example, hyperlipidemia, obesity, atherosclerosis or type II diabetes.

Apo B-48, synthetized by the intestine, is necessary for the assembly of chylomicrons and therefore has an obligatory role in the intestinal absorption of dietary fats. The present invention provides biphenylcarboxamide compounds which are acting as selective MTP inhibitors at the level of the gut wall.

Additionally the present invention provides pharmaceutical compositions comprising at least one pharmaceutically acceptable carrier and a therapeutically effective amount of a biphenylcarboxamide compound having the formula (I).

In order to prepare the pharmaceutical compositions of this invention, an effective amount of the particular compound, in base or addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1 ',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The biphenylcarboxamide compounds of this invention may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use. The biphenylcarboxamide compounds of this invention may also be formulated in rectal compositions such as suppositories or retention enemas, e.g. containing conventional suppository bases such as cocoa butter and/or other glycerides.

The biphenylcarboxamide compounds of this invention may be used in conjunction with other pharmaceutical agents, in particular the pharmaceutical compositions of the present invention may further comprise at least one additional lipid-lowering agent, thus leading to a so-called combination lipid-lowering therapy. The said additional lipid-lowering agent may be, for instance, a known drug conventionally used for the management of hyperlipidaemia such as e.g. a bile acid sequestrant resin, a fibric acid derivative or nicotinic acid as previously mentioned in the background of the invention. Suitable additional lipid-lowering agents also include other cholesterol biosynthesis inhibitors and cholesterol absorption inhibitors, especially HMG-CoA reductase inhibitors and HMG-CoA synthase inhibitors, HMG-CoA reductase gene expression inhibitors, CETP inhibitors, ACAT inhibitors, squalene synthetase inhibitors and the like.

Any HMG-CoA reductase inhibitor may be used as the second compound in the combination therapy aspect of this invention. The term "HMG-CoA reductase inhibitor" as used herein, unless otherwise stated, refers to a compound which inhibits the biotransformation of hydroxymethylglutaryl-coenzyme A to mevalonic acid as catalyzed by the enzyme HMG-CoA reductase. Such inhibition may be determined readily by one skilled in the art according to standard assays, i.e. Methods of Enzymology (1981) 71:455–509. Exemplary compounds are described e.g. in U.S. Pat. No. 4,231,938 (including lovastatin), U.S. Pat. No. 4,444,784 (including simvastatin), U.S. Pat. No. 4,739,073 (including fluvastatin), U.S. Pat. No. 4,346,227 (including pravastatin), EP-A-491,226 (including rivastatin) and U.S. Pat. No. 4,647,576 (including atorvastatin).

Any HMG-CoA synthase inhibitor may be used as the second compound in the combination therapy aspect of this invention. The term "HMG-CoA synthase inhibitor" as used herein, unless otherwise stated, refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one skilled in the art according to standard assays, i.e. Methods of Enzymology (1985)110:19–26. Exemplary compounds are described e.g. in U.S. Pat. No. 5,120,729 relating to beta-lactam derivatives, U.S. Pat. No. 5,064,856 relating to spiro-lactone derivatives and U.S. Pat. No. 4,847,271 relating to oxetane compounds.

Any HMG-CoA reductase gene expression inhibitor may be used as the second compound in the combination therapy aspect of this invention. These agents may be HMG-CoA reductase trancription inhibitors that block the transcription of DNA or translation inhibitors that prevent translation of mRNA coding for HMG-CoA reductase into protein. Such inhibitors may either affect trancription or translation directly or may be biotransformed into compounds having the above-mentioned attributes by one or more enzymes in the cholesterol biosynthetic cascade or may lead to accumulation of a metabolite having the above-mentioned activities. Such regulation may be determined readily by one skilled in the art according to standard assays, i.e. Methods of Enzymology (1985) 110:9–19. Exemplary compounds are described e.g. in U.S. Pat. No. 5,041,432 and E. I. Mercer, *Prog. Lip. Res.* (1993) 32:357–416.

Any CETP inhibitor may be used as the second compound in the combination therapy aspect of this invention. The term "CETP inhibitor" as used herein, unless otherwise stated, refers to a compound which inhibits the cholesteryl ester transfer protein (CETP) mediated transport of various cholesteryl esters and triglycerides from HDL to LDL and VLDL. Exemplary compounds are described e.g. in U.S. Pat. No. 5,512,548, in *J. Antibiot.* (1996) 49(8):815–816 and *Bioorg.Med.Chem.Lett.* (1996) 6:1951–1954.

Any ACAT inhibitor may be used as the second compound in the combination therapy aspect of this invention. The term "ACAT inhibitor" as used herein, unless otherwise stated, refers to a compound which inhibits the intracellular esterification of dietary cholesterol by the enzyme acyl CoA:cholesterol acyltransferase. Such inhibition may be determined readily by one skilled in the art according to standard assays, i.e. the method of Heider et al., *Journal of Lipid Research* (1983) 24:1127. Exemplary compounds are described e.g. in U.S. Pat. No. 5,510,379, in WO 96/26948 and WO 96/10559.

Any squalene synthetase inhibitor may be used as the second compound in the combination therapy aspect of this invention. The term "squalene synthetase inhibitor" as used herein, unless otherwise stated, refers to a compound which inhibits the condensation of two molecules of farnesylpyrophosphate to form squalene, catalyzed by the enzyme squalene synthetase. Such inhibition may be determined readily by one skilled in the art according to standard methods, i.e. Methods of Enzymology (1985) 110:359–373. Exemplary compounds are described e.g. in EP-A-567,026, in EP-A-645,378 and in EP-A-645,377.

Those of skill in the treatment of hyperlipidemia will easily determine the therapeutically effective amount of a biphenylcarboxamide compound of this invention from the test results presented hereinafter. In general it is contemplated that a therapeutically effective dose will be from about 0.001 mg/kg to about 5 mg/kg of body weight, more preferably from about 0.01 mg/kg to about 0.5 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 350 mg, more particularly from about 1 to about 200 mg, of the active ingredient per unit dosage form.

The exact dosage and frequency of administration depends on the particular biphenylcarboxamide compound of formula (I) used, the particular condition being treated, the severity of the condition being treated, the age, weight and general physical condition of the particular patient as well as the other medication (including the above-mentioned additional lipid-lowering agents), the patient may be taking, as is well known to those skilled in the art. Furthermore, said effective daily amount may be lowered or increased depending on the response of the treated patient and/or depending on the evaluation of the physician prescribing the biphenylcarboxamide compounds of the instant invention. The effective daily amount ranges mentioned hereinabove are therefore only guidelines.

Experimental Part

In the procedures described hereinafter the following abbreviations were used: "ACN" stands for acetonitrile; "THF" stands for tetrahydrofuran; "DCM" stands for dichloromethane; "DIPE" stands for diisopropylether; "DMF" means N,N-dimethyl-formamide; "NMP" means N-methyl-2-pyrrolidone; "TFA" means trifluoroacetic acid; "TIS" means triisopropylsilane; "DIPEA" means diisopropylethylamine; "MIK" means methyl isobutyl ketone; "BINAP" means 2,2'-bis(diphenylphosphino)-1,1'-binaphthyl; and "TMSOTf" means trimethylsilyl triflate.

A. Synthesis of the Intermediates

For the combinatorial approach a number intermediate resins were prepared starting from a commercially available resin:

Scheme 2:

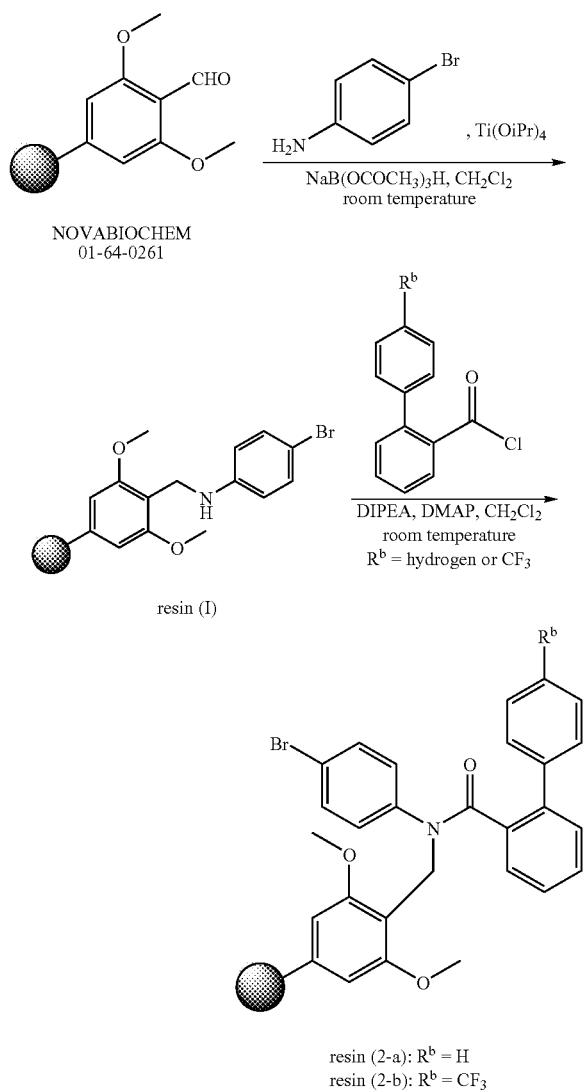

resin (2-a): $R^b$ = H
resin (2-b): $R^b$ = $CF_3$

EXAMPLE A. 1

A mixture of Novabiochem 01-64-0261 commercial resin (25.1 g), 4-bromoaniline (24 g) and titanium (IV) isopropoxide (41 ml) in DCM (400 ml) was stirred gently for one hour at room temperature. Sodium triacetoxyborohydride (30 g) was added and the reaction mixture was stirred overnight at room temperature. Methanol (50 ml) was added and the mixture was stirred for one hour, then filtered, washed once with DCM, once with methanol, then once with DCM (200 ml)+DIPEA (20 ml), washed three times with firstly DCM, followed secondly by methanol, then dried, yielding 29.28 g of a resin identified as resin(1) in scheme 2, which is used in the next reaction step without further purification.

EXAMPLE A.2

2-Phenyl benzoic acid (8.3 g) was dissolved in DCM (100 ml). Thionyl chloride (10 g) was added. DMF (10 drops) was added and the mixture was stirred and refluxed for one hour. The solvent was evaporated. DCM (three times 50 ml) was added to the residue and the solvent was evaporated. The residue was dissolved in DCM (50 ml). This solution was added to a mixture of the resin (1) of example A.1 (14.64 g), DIPEA (24 ml) and 4-dimethylaminopyridine (hereinafter referred as DMAP) (0.5 g) in DCM (150 ml). The reaction mixture was shaken overnight at room temperature, then filtered and the filter residue was washed with 100 ml DMF+20 ml DIPEA, then with methanol, water, DCM, methanol, DCM and methanol, and dried, yielding 15.73 g of a resin identified as resin (2-a) in scheme 2.

EXAMPLE A.3

4'-(Trifluoromethyl)-2-biphenyl carboxylic acid (14.64 g) was dissolved in DCM (100 ml). DMF (1 ml) was added. Thionyl chloride (10 g) was added and the mixture was stirred and refluxed for one hour. The solvent was evaporated. DCM (twice 50 ml) was added, then the solvent was evaporated. The residue was dissolved in DCM (50 ml). This solution was added to a mixture of the resin (1) of example A.1 (14.64 g), DIPEA (24 ml) and DMAP (0.5 g) in DCM (150 ml). The reaction mixture was shaken for four hours at room temperature then filtered and the filter residue was washed with 100 ml DMF+20 ml DIPEA, then washed three times firtstly with DCM and secondly with methanol, and finally dried. This reaction product was reacted once more with half the initial quantities of 4'-(trifluoromethyl)-2-biphenyl carboxylic acid, thionyl chloride, DIPEA and DMAP. The reaction mixture was shaken overnight at room temperature, then filtered, and the filter residue was shaken with DMF+20 ml DIPEA, then methanol, water, methanol, DCM, methanol, DCM+methanol, then dried, yielding 17.48 g of a resin identified as resin (2-b) in scheme 2.

EXAMPLE A.4 a) A solution of 4'-(trifluoromethyl)-[1,1'-biphenyl]-2-carbonyl chloride (0.019 mol) in DCM (50 ml) was added slowly at 5° C. to a mixture of 1-amino-4-iodo-benzene (0.017 mol) and triethylamine (0.026 mol) in DCM (40 ml). The mixture was stirred at room temperature for 1 hour, then washed with HCl 1N, then with $K_2CO_3$ 10%. The organic layer was separated, dried, filtered, and the solvent was evaporated. The residue was crystallized from DIPE. The precipitate was filtered off and dried, yielding 6.1 g of N-(4-iodophenyl)-4'-(trifluoromethyl)-[1,1'-biphenyl]-2-carboxamide (intermediate 1; mp. 147° C.).

b) A mixture of intermediate (1) (0.012 mol), N-allylphthalimide (0.012 mol), palladium(II) acetate (0.001 mol) and triethylamine (0.024 mol) was stirred at 100° C. for 12 hours in a bomber, then dissolved in DCM and washed with $K_2CO_3$ 10%. The organic layer was separated, dried, filtered, and the solvent was evaporated. The residue was crystallized from ACN. The precipitate was filtered off and dried, yielding 3.2 g of N-[4-[(1E)-3-(1,3-dihydro-1,3-dioxo-2H-isoindol-2-yl)-1-propenyl]phenyl]-4'-(trifluoromethyl)-[1,1'-biphenyl]-2-carboxamide (intermediate 2; mp. 190° C.).

c) A mixture of intermediate (2) (0.005 mol) and an aqueous hydrazine solution (0.005 mol) in ethanol (30 ml) was stirred and refluxed for 2 hours. The precipitate was filtered and washed with ethanol. Water was added. The suspension was basified with NaOH and filtered over celite. Celite was washed with ethyl acetate. The filtrate was extracted with ethyl acetate and washed with $K_2CO_3$, then with NaCl. The organic layer was separated, dried, filtered, and the solvent was evaporated. The residue was crystallized from ACN. The precipitate was filtered off and dried, yielding 2.5 g of N-[4-[(1E)-3-amino-1-propenyl]phenyl]-4'-(trifluoromethyl)-[1,1'-biphenyl]-2-carboxamide (intermediate 3; mp. 190° C.).

B. Synthesis of the Final Compounds

EXAMPLE B.1

A suspension of BINAP (0.00014 mol) in NMP (1 ml) was added to resin (2-b) (0.00014 mol) and sodium tert-butoxide (0.00252 mol). 1,2-Diaminoethane (0.0021 mol) in NMP (2 ml) was added and the mixture was stirred under argon. $Pd_2(dba)_3$ (0.000028 mol) in NMP (1 ml) was added and the reaction mixture was shaken for 19 hours at 105° C. The mixture was cooled, filtered and the filter residue was washed with DMF, water, DMF (3×), water (3×), DMF (3×), $CH_3OH$ (3×), DCM (3×), $CH_3OH$ (3×) and NMP (2×). NMP (3 ml) was added. Methyl 2-bromo-2-phenylacetate (0.0007 mol) in NMP (1 ml) was added. DIPEA (0.3 ml) was added and the reaction mixture was shaken for 18 hours at room temperature. The reaction mixture was filtered, washed with DMF and water, then with DMF (3×), water (3×), DMF (3×), $CH_3OH$ (3×), DCM (3×), $CH_3OH$ (3×) and DCM (3×). A solution of TFA/TIS/DCM (49:2:49) (4 ml) was added and the mixture was shaken for one hour at room temperature. The mixture was filtered and more TFA/TIS/DCM (49:2:49) (1.5 ml) was added. The mixture was shaken for 15 minutes, filtered, washed with DCM (2 ml), then the filtrates were blown dry under nitrogen. The residue was purified by HPLC over Purospher Star RP-18 (20 g, 5 µm; eluent: ((0.5% $NH_4OAc$ in $H_2O$)/$CH_3CN$ 90/10)/$CH_3OH$/$CH_3CN$ (0 min) 75/25/0, (10.00 min) 0/50/50, (16.00 min) 0/0/100, (18.10–20 min) 75/25/0). The desired fractions were collected and the organic solvent was evaporated. The aqueous concentrate was treated with an aqueous $Na_2CO_3$ solution, then extracted with DCM. The extract was separated through Extrelut and the filtrates were blown dry under nitrogen at 50° C. The residue was dried further (vacuum, 50° C.), yielding 0.006 g of compound 1.

Compounds identified as No. 2 to No. 29 in the following table F-1 were similarly prepared while using the same experimental procedure and replacing 1,2-diaminoethane by the appropriate reactive diamine.

EXAMPLE B.2

NMP (2 ml) was added to resin (2-a) (0.00014 mol). BINAP (0.00014 mol) and sodium tert-butoxide (0.00252 mol) were added. 1,2-Diaminoethane (0.0021 mol) in NMP (1 ml) was added and the mixture was shaken for 1 hour under argon. $Pd_2(dba)_3$ (0.000028 mol) in NMP (1 ml) was added and the reaction mixture was shaken for 18 hours at 105° C. The mixture was cooled, filtered and the filter residue was washed with DMF-water 50—50, DMF (3×), water (3×), DMF (3×), $CH_3OH$ (3×), DCM (3×), $CH_3OH$ (3×) and NMP (2×). NMP (3 ml) was added. Methyl 2-bromo-2-phenylacetate (0.0007 mol) in NMP (1 ml) was added. DIPEA (0.300 ml) was added and the mixture was shaken for 18 hours at room temperature. The mixture was filtered, washed with DMF and water, washed with DMF (3×), water (3×), DMF (3×), $CH_3OH$ (3×), DCM (3×), $CH_3OH$ (3×), DCM (3×). TFA/TIS/DCM (49:2:49) (4 ml) was added and the mixture was shaken for 2 hours at room temperature, then filtered. More TFA/TIS/DCM (49:2:49) (2 ml) was added and the reaction mixture was shaken for 15 minutes, then filtered. The filter residue was washed with DCM (2 ml), then the filtrates were blown dry under nitrogen. The residue was purified by HPLC over Purospher Star RP-18 (20 g, 5 µm; eluent: ((0.5% $NH_4OAc$ in $H_2O$)/$CH_3CN$ 90/10)/$CH_3OH$/$CH_3CN$ (0 min) 75/25/0, (10.00 min) 0/50/50, (16.00 min) 0/0/100, (18.10–20 min) 75/25/0). The desired fractions were collected and the organic solvent was evaporated. The aqueous concentrate was treated with an aqueous $Na_2CO_3$ solution, then extracted with DCM. The extract was separated and the filtrates were blown dry under nitrogen at 50° C. The residue was dried further (vacuum, 50° C.), yielding 0.007 g of compound 30.

Compounds identified as No. 31 to No. 58 in the following table F-1 were similarly prepared while using the same experimental procedure and replacing 1,2-diaminoethane by the appropriate reactive diamine.

EXAMPLE B.3

NMP (2 ml) was added to resin (2-a) (0.00014 mol). BINAP (0.00014 mol) and sodium tert-butoxide (0.00252 mol) were added portionwise. 4-Amino-1-tert-butoxycarbonylpiperidine (0.0021 mol) in NMP (1 ml) was added and the mixture was shaken for 1 hour under nitrogen. $Pd_2(dba)_3$ (0.000028 mol) in NMP (1 ml) was added and the reaction mixture was shaken for 18 hours at 105° C. The mixture was cooled, filtered and the filter residue was washed with DMF-water 50—50, DMF (3×), water (3×), DMF (3×), $CH_3OH$ (3×), DCM (3×), $CH_3OH$ (3×) and DCM (3×). TMSOTf (1 M) and 2,6-lutidine (1.5 M) in DCM (3 ml) was added and the mixture was shaken for 2 hours at room temperature. The mixture was filtered, washed with DCM (3×), and methanol (4 ml) was added. The mixture was shaken for one hour at room temperature, filtered and the filter residue was washed with DCM (3×), $CH_3OH$ (3×), DCM (3×), $CH_3OH$ (3×), DCM (3×), $CH_3OH$ (3×), and once with NMP. NMP (3 ml) was added. Ethyl 2-bromo-2-phenylacetate (0.0007 mol) in NMP (1 ml) was added. DIPEA (0.3 ml) was added and the reaction mixture was shaken for 20 hours at room temperature. The reaction mixture was filtered, washed three times with DMF, 3× with water, 3×DMF, 3×$CH_3OH$, 3×DCM, 3×$CH_3OH$ and 3×DCM. TFA/TIS/DCM (49:2:49) (4 ml) was added and the mixture was shaken for one hour at room temperature, then filtered. More TFA/TIS/DCM (49:2:49) (2 ml) was added and the mixture was shaken for 30 minutes, then filtered, and washed with DCM (2 ml). The filtrates were blown dry under nitrogen at 50° C. The residue was purified by HPLC over Purospher Star RP-18 (20 g, 5 µm; eluent: ((0.5% $NH_4OAc$ in $H_2O$)/$CH_3CN$ 90/10)/$CH_3OH$/$CH_3CN$ (0 min) 75/25/0, (10.00 min) 0/50/50, (16.00 min) 0/0/100, (18.10–20 min) 75/25/0). The desired fractions were collected and the organic solvent was evaporated. The aqueous concentrate was treated with an aqueous $Na_2CO_3$ solution, then extracted with DCM. The extract was separated and the filtrates were blown dry under nitrogen at 50° C. The residue was dried further (vacuum, 55° C.), yielding 0.007 g of compound 59.

Compounds identified as No. 60 to No. 96 in the following table F-1 were similarly prepared while using the same experimental procedure and replacing 4-amino-1-tert-butoxycarbonylpiperidine by the appropriate reactive amine.

EXAMPLE B.4

Resin (2-b) (0.00014 mol) was washed with NMP (2 ml). BINAP (0.00014 mol) and sodium tert-butoxide (0.00252 mol) were added. 4-Amino-1-tert-butoxycarbonylpiperidine (0.0021 mol) in NMP (1 ml) was added. NMP (3 ml) was added and the mixture was shaken for 1 hour under argon. $Pd_2(dba)_3$ (0.000028 mol) in NMP (1 ml) was added and the reaction mixture was shaken for 18 hours at 105° C. The mixture was cooled, filtered and the filter residue was washed with DMF, DMF-water 50—50, DMF (3×), water (3×), DMF (3×), $CH_3OH$ (3×), DCM (3×), $CH_3OH$ (3×) and DCM (3×). TMSOTf (1 M) and 2,6-lutidine (1.5 M) in DCM (3 ml) was added and the mixture was shaken for 2 hours at room temperature. The mixture was filtered, washed with DCM (3×), $CH_3OH$ (3×), DCM (3×), $CH_3OH$ (3×), DCM (3×), $CH_3OH$ (3×), then with NMP (2×). NMP (3 ml) was added. Methyl 2-bromo-2-phenylacetate (0.160 g) in NMP (1 ml) was added. DIPEA (0.3 ml) was added. The reaction mixture was shaken for 20 hours at room temperature, filtered, washed with DMF, then DMF-water 50—50, then with DMF (3×), water (3×), DMF (3×), $CH_3OH$ (3×), DCM (3×), $CH_3OH$ (3×), and DCM (3×). TFA/TIS/DCM (49:2:49) (4 ml) was added and the mixture was shaken for one hour, then filtered. More TFA/TIS/DCM (49:2:49) (2 ml) was added and the reaction mixture was shaken for 30 minutes, then filtered. The filtrates were blown dry under nitrogen at 50° C. The residue was purified by HPLC over Purospher Star RP-18 (20 g, 5 µm; eluent: ((0.5% $NH_4OAc$ in water)/$CH_3CN$ 90/10)/$CH_3OH$/$CH_3CN$ (0 min) 75/25/0, (10.00 min) 0/50/50, (16.00 min) 0/0/100, (18.10–20 min) 75/25/0). The desired fractions were collected and the organic solvent was evaporated. The aqueous concentrate was treated with an aqueous $Na_2CO_3$ solution, then extracted with DCM. The extract was separated and the filtrates were blown dry under nitrogen at 50° C. The residue was dried further (vacuum, 50° C.), yielding 0.031 g of compound 97.

Compounds identified as No. 98 to No.136 in the following table F-1 were similarly prepared while using the same experimental procedure and replacing 4-amino-1-tert-butoxycarbonylpiperidine by the appropriate reactive amine.

EXAMPLE B.5

A mixture of intermediate (3) (0.006 mol), methyl 2-bromo-2-phenylacetate (0.011 mol), triethylamine (1.6 ml) and tetrabutylammonium iodide (0.001 mol) in THF (20 ml) was stirred at room temperature for 8 hours. Water was added. The mixture was extracted with ethyl acetate. The organic layer was separated, dried, filtered, and the solvent was evaporated. The residue was purified by column chromatography over silica gel (eluent: $CH_2Cl_2$/$CH_3OH$ 98.5/1.5) and crystallized from diethyl ether, yielding compound (137), mp. 142° C.

Table F-1 lists the compounds that were prepared according to one of the above Examples. The following abbreviations were used in the tables: $.C_2HF_3O_2$ stands for the trifluoroacetate salt.

TABLE F-1

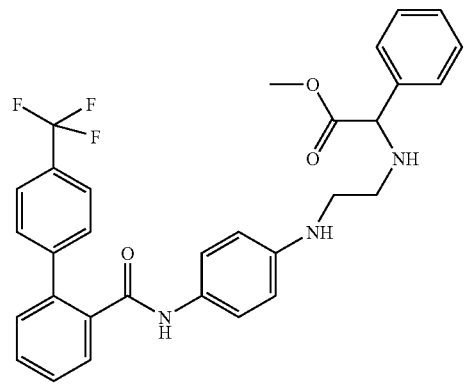

Co. No. 1; Ex. B.1

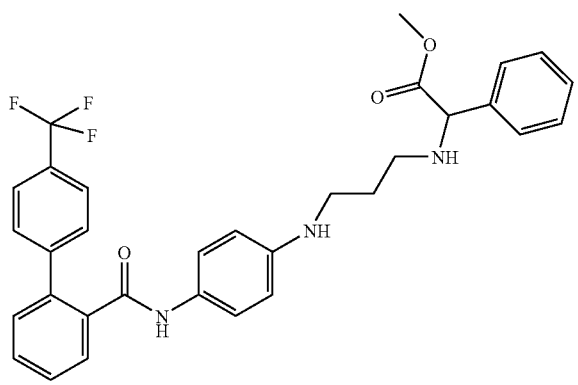

Co. No. 2; Ex. B.1

TABLE F-1-continued
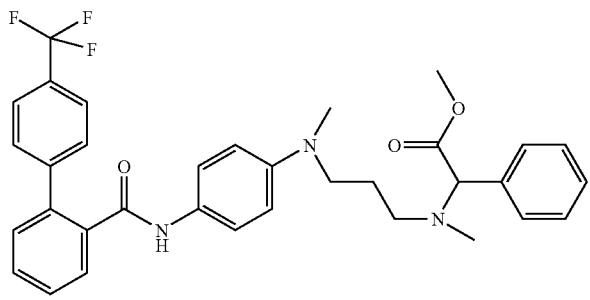
Co. No. 3; Ex. B.1
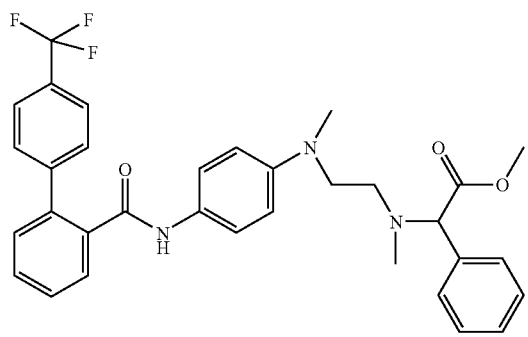
Co. No. 4; Ex. B.1
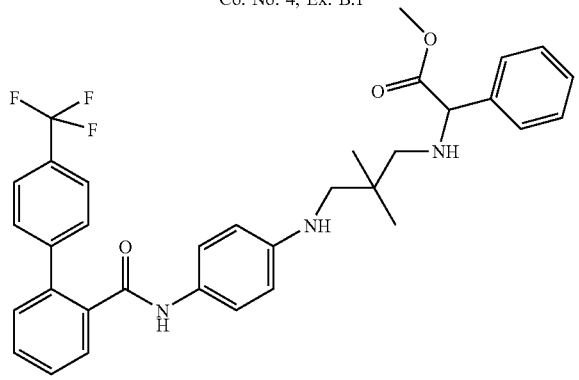
Co. No. 5; Ex. B.1
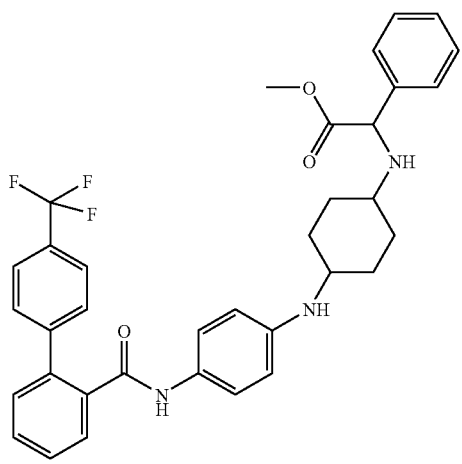
(TRANS); Co. No. 6; Ex. B.1

TABLE F-1-continued
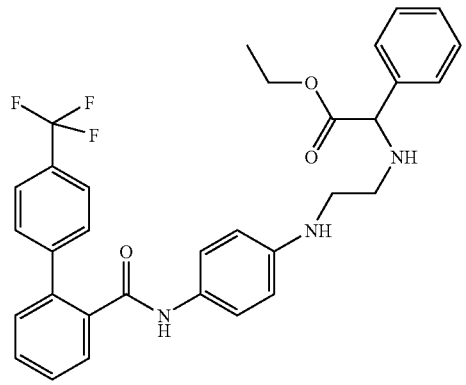
Co. No. 7; Ex. B.1
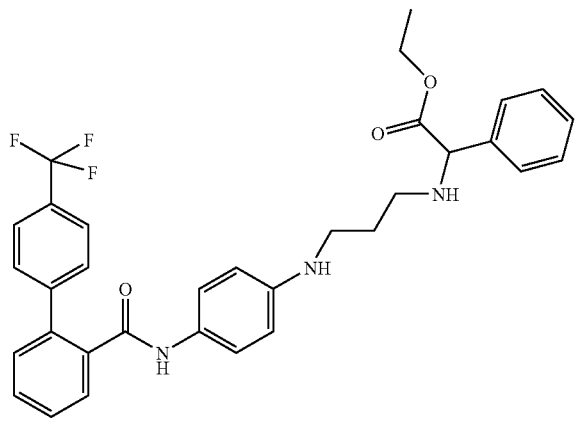
Co. No. 8; Ex. B.1
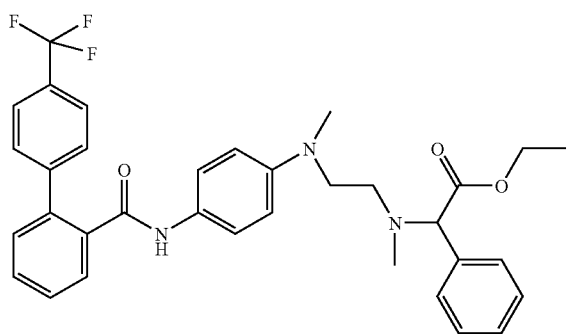
Co. No. 9; Ex. B.1

TABLE F-1-continued
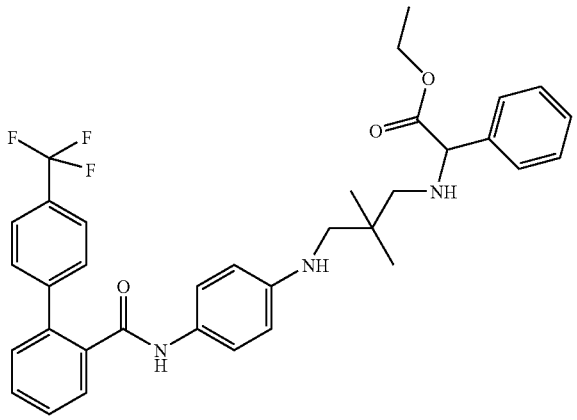
Co. No. 10; Ex. B.1
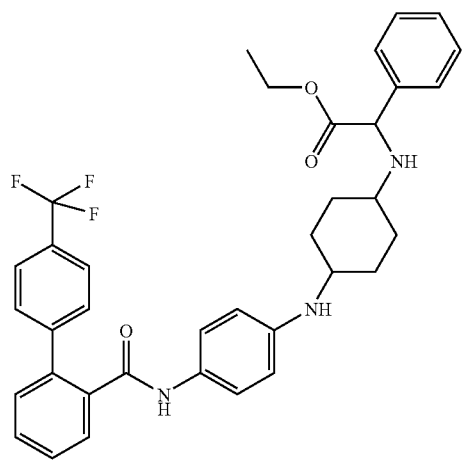
(TRANS); Co. No. 11; Ex. B.1
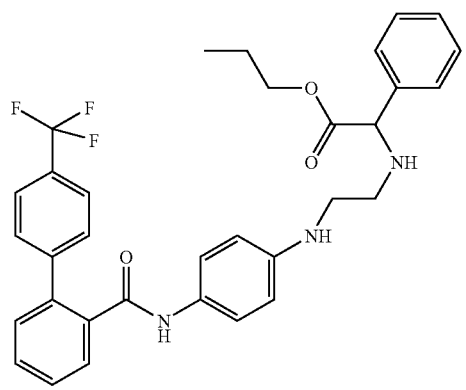
Co. No. 12; Ex. B.1

TABLE F-1-continued
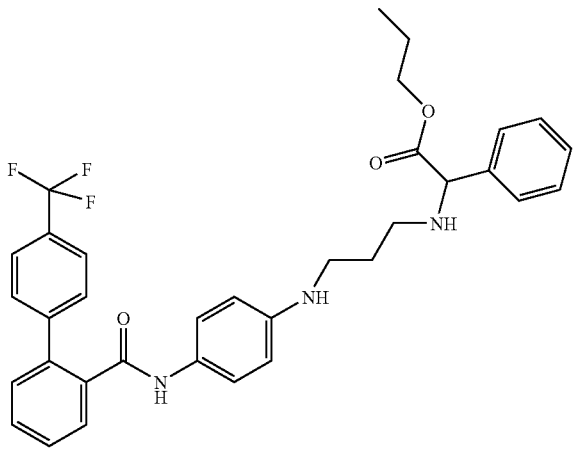
Co. No. 13; Ex. B.1
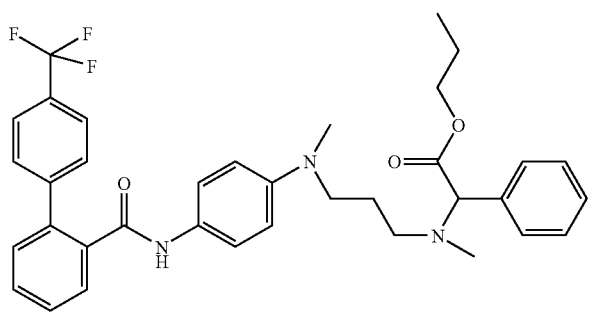
Co. No. 14; Ex. B.1
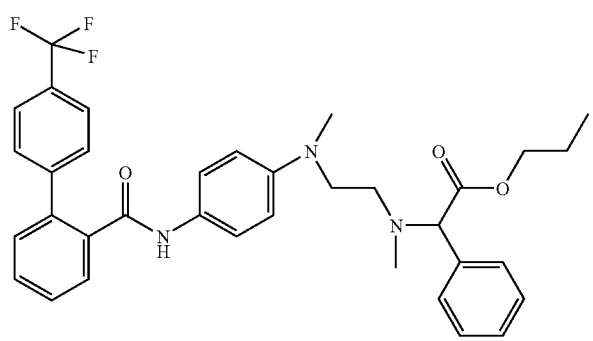
Co. No. 15; Ex. B.1

TABLE F-1-continued
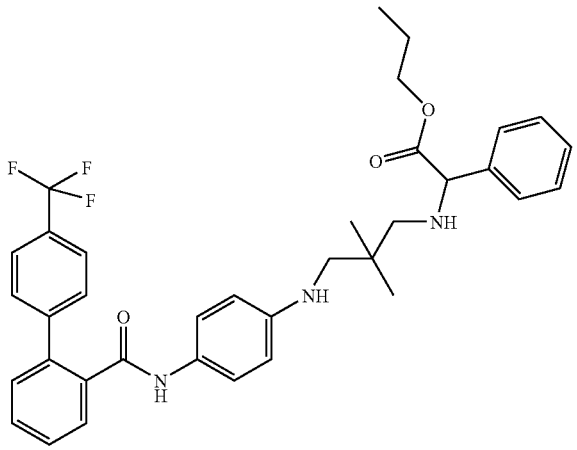
Co. No. 16; Ex. B.1
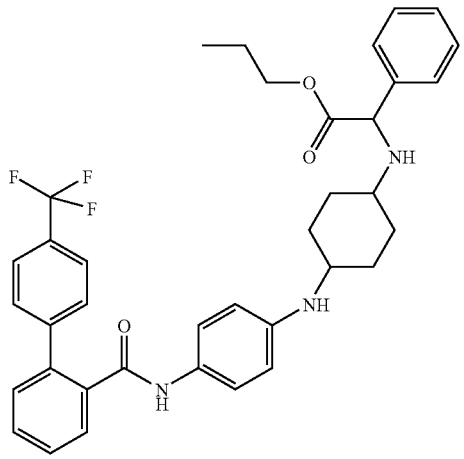
(TRANS); Co. No. 17; Ex. B.1
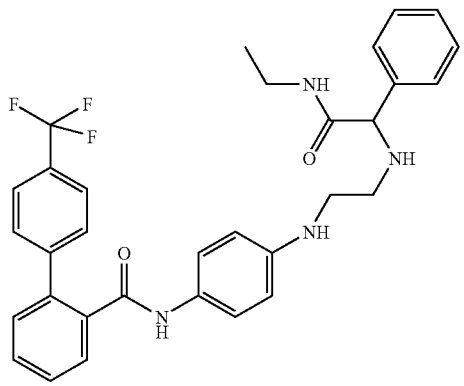
Co. No. 18; Ex. B.1

TABLE F-1-continued
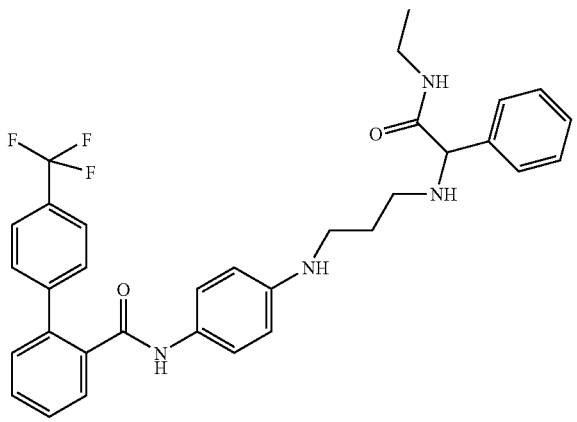
Co. No. 19; Ex. B.1
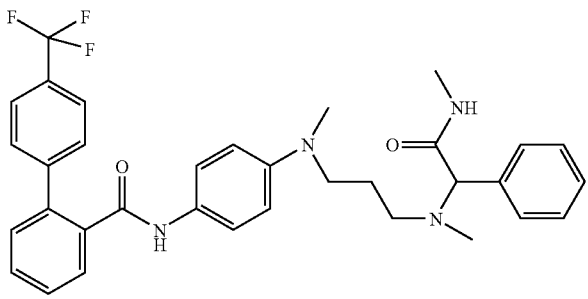
Co. No. 20; Ex. B.1
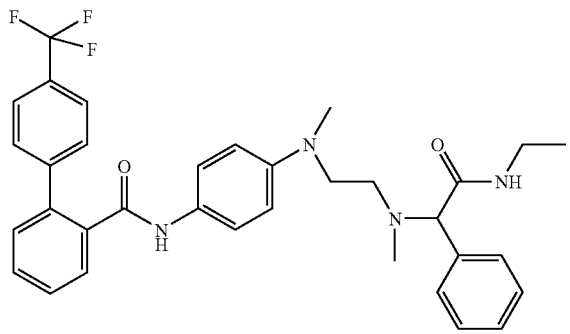
Co. No. 21; Ex. B.1
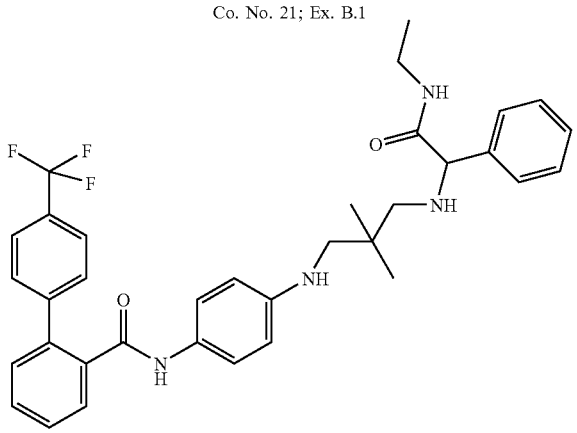
Co. No. 22; Ex. B.1

TABLE F-1-continued
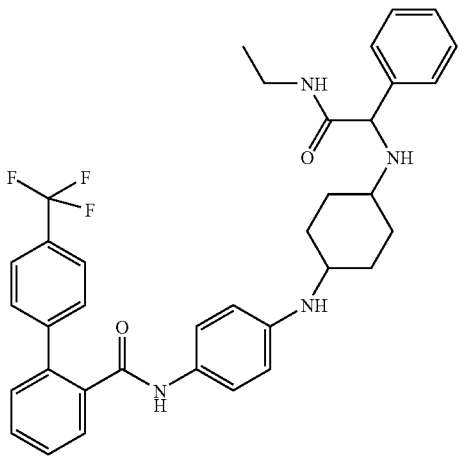
(TRANS); Co. No. 23; Ex. B.1
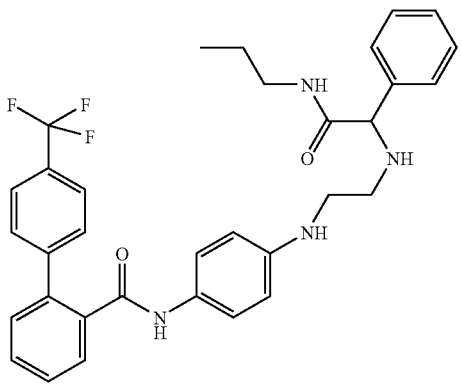
Co. No. 24; Ex. B.1
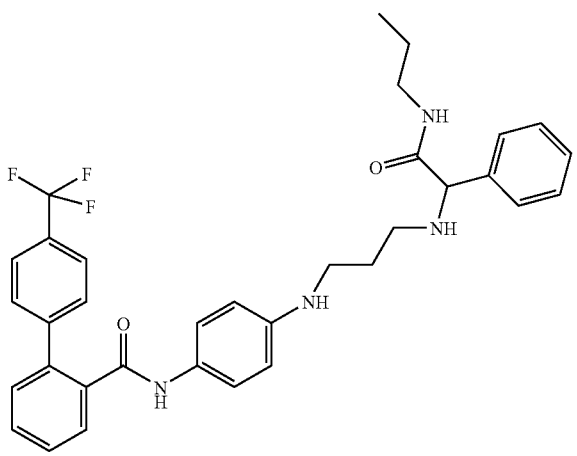
Co. No. 25; Ex. B.1

TABLE F-1-continued
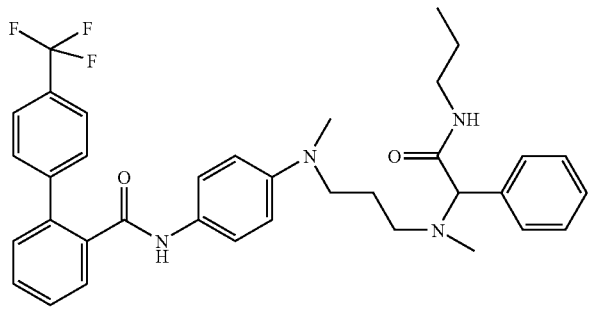
Co. No. 26; Ex. B.1
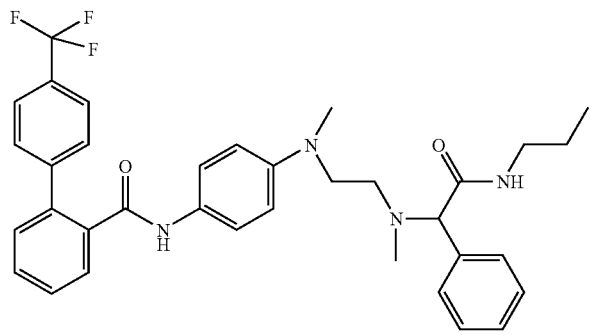
Co. No. 27; Ex. B.1
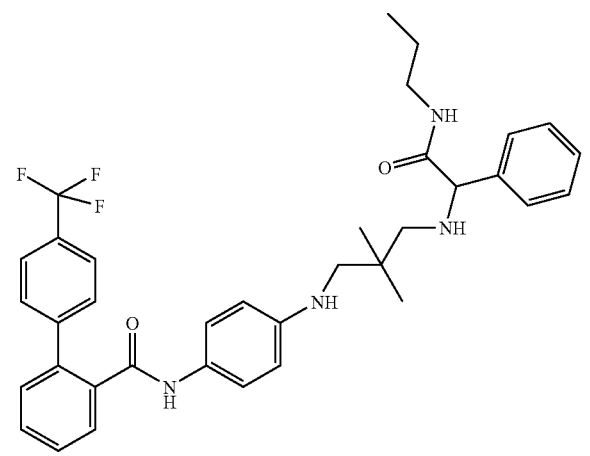
Co. No. 28; Ex. B.1

TABLE F-1-continued
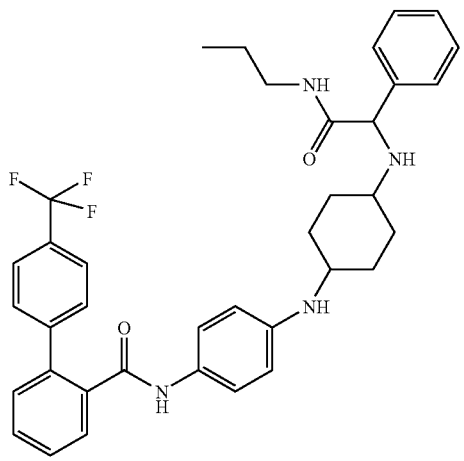
(TRANS); Co. No. 29; Ex. B.1
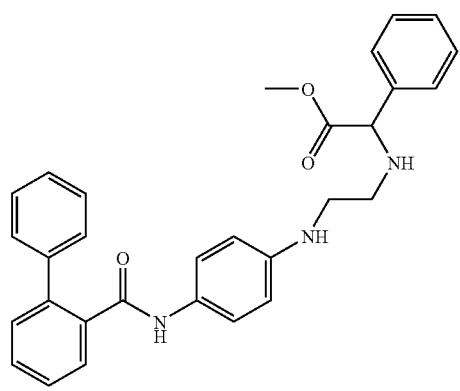
Co. No. 30; Ex. B.2
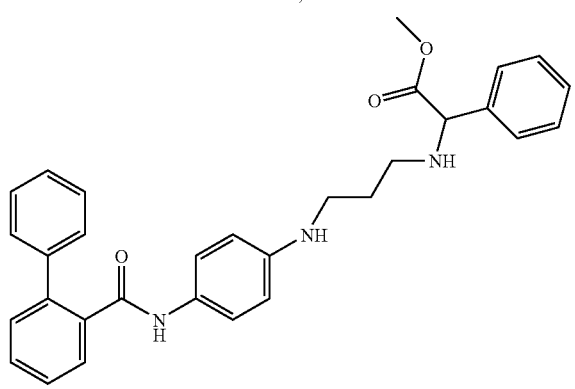
Co. No. 31; Ex. B.2
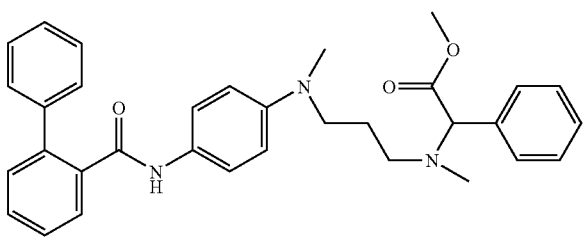
Co. No. 32; Ex. B.2

TABLE F-1-continued
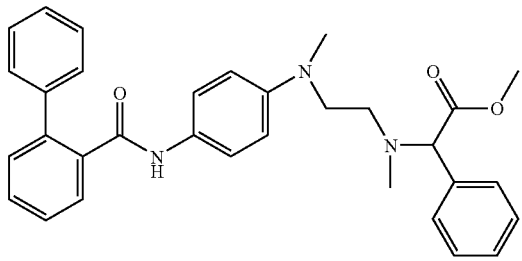
Co. No. 33; Ex. B.2
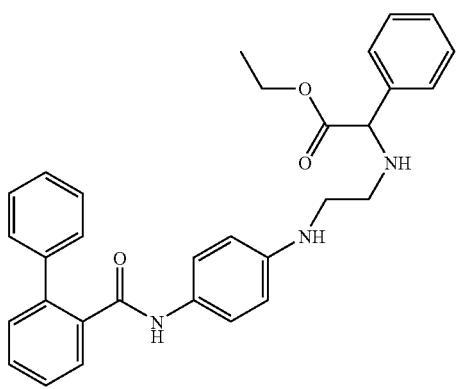
Co. No. 34; Ex. B.2
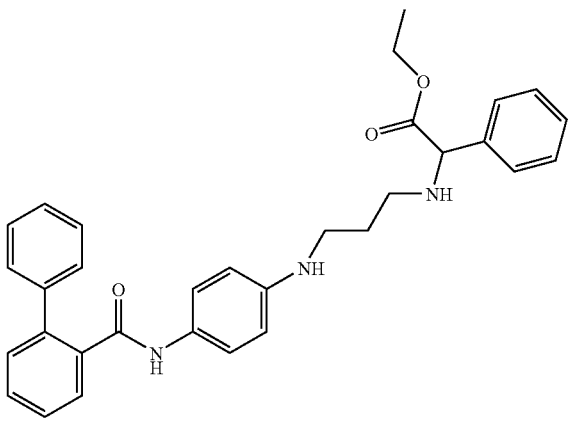
Co. No. 35; Ex. B.2
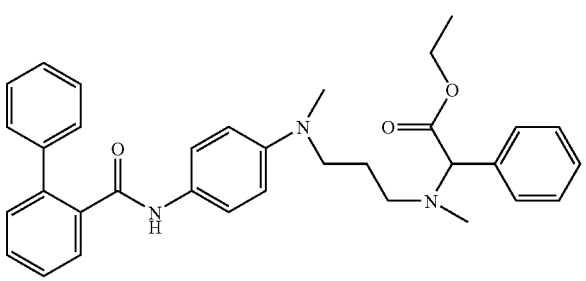
Co. No. 36; Ex. B.2

TABLE F-1-continued
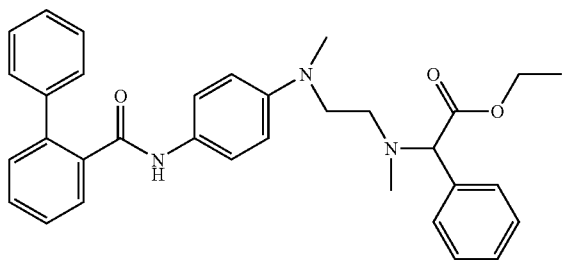
Co. No. 37; Ex. B.2
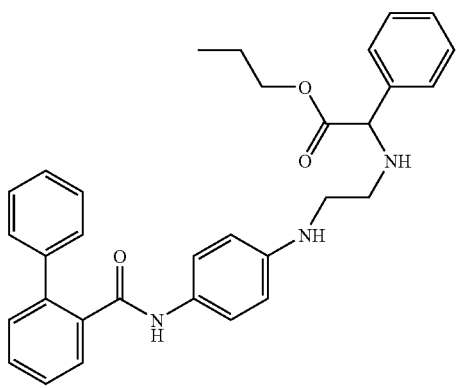
Co. No. 38; Ex. B.2
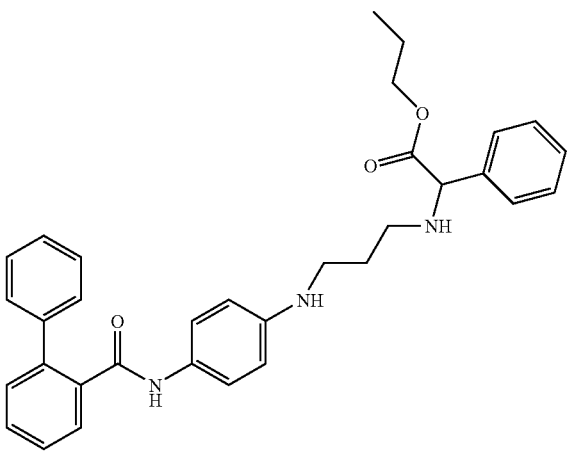
Co. No. 39; Ex. B.2
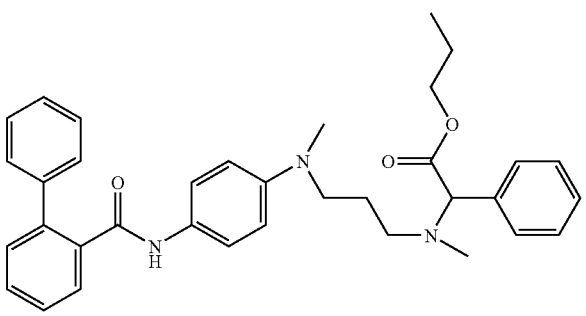
Co. No. 40; Ex. B.2

TABLE F-1-continued
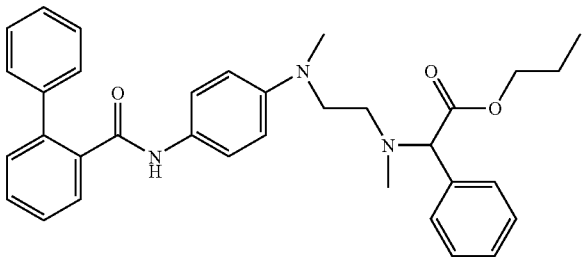
Co. No. 41; Ex. B.2
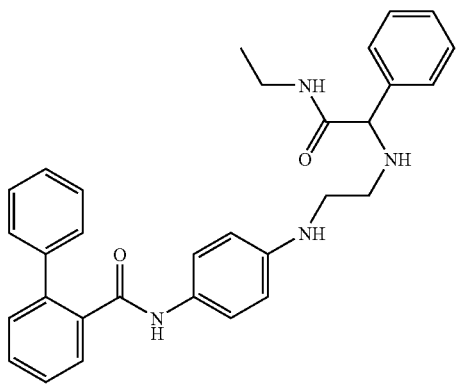
Co. No. 42; Ex. B.2
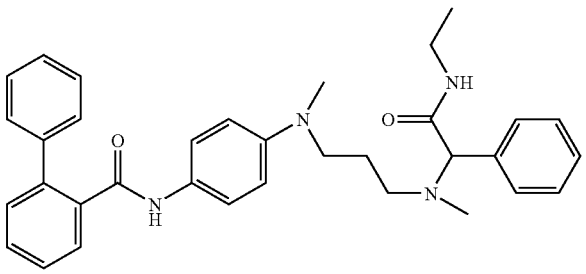
Co. No. 43; Ex. B.2
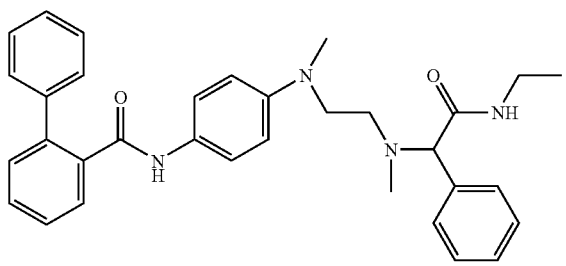
Co. No. 44; Ex. B.2

TABLE F-1-continued
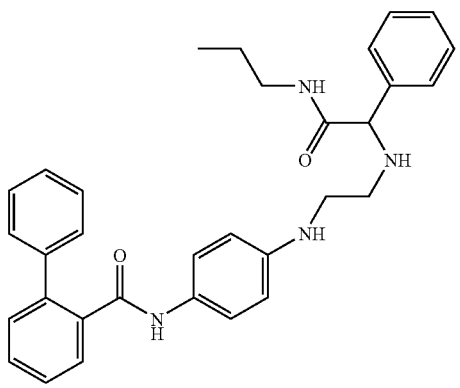
Co. No. 45; Ex. B.2
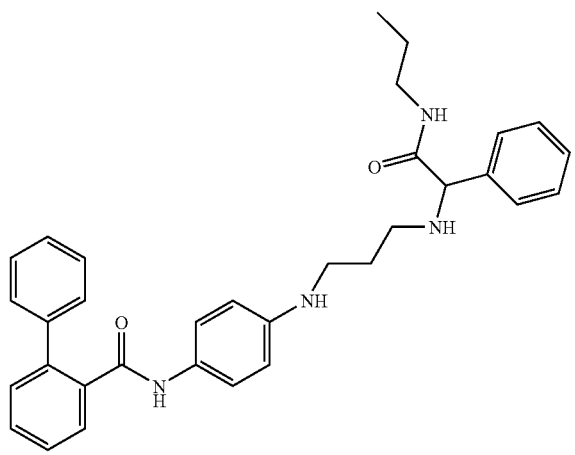
Co. No. 46; Ex. B.2
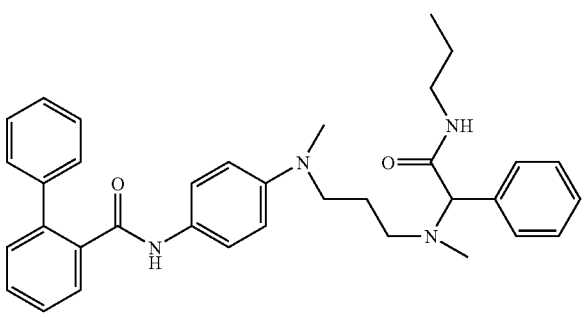
Co. No. 47; Ex. B.2
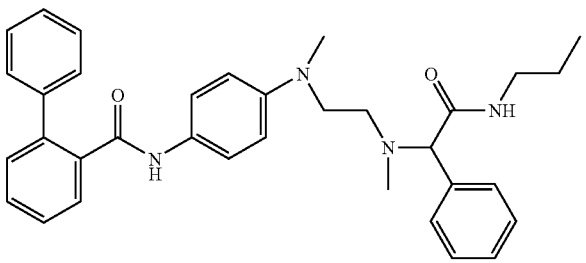
Co. No. 48; Ex. B.2

TABLE F-1-continued
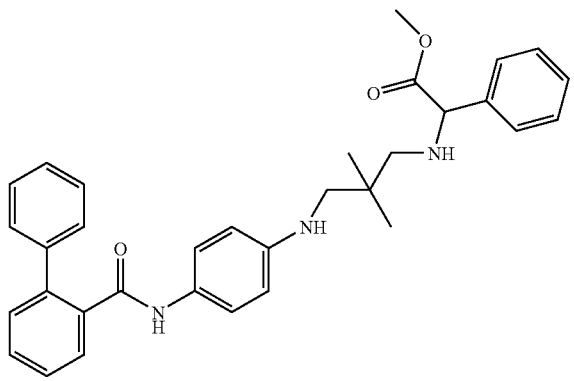
Co. No. 49; Ex. B.2
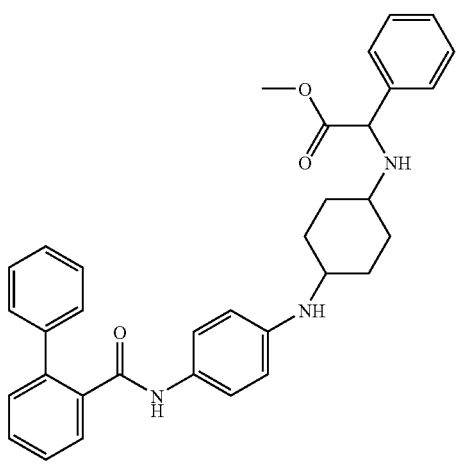
(TRANS); Co. No. 50; Ex. B.2
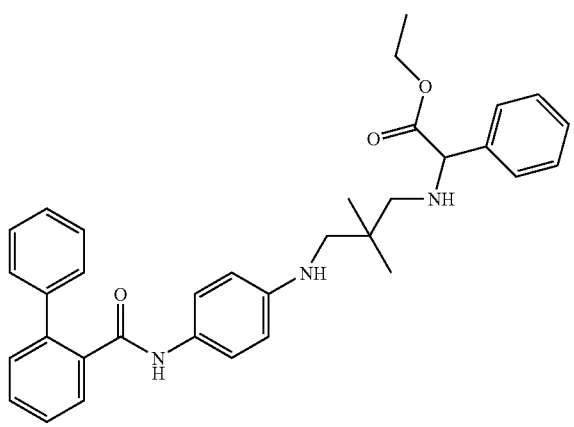
Co. No. 51; Ex. B.2

TABLE F-1-continued
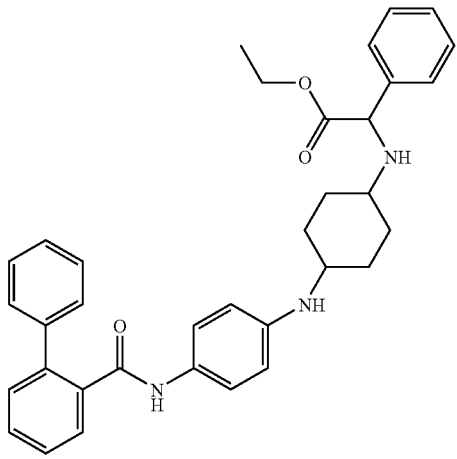
Co. No. 52; Ex. B.2
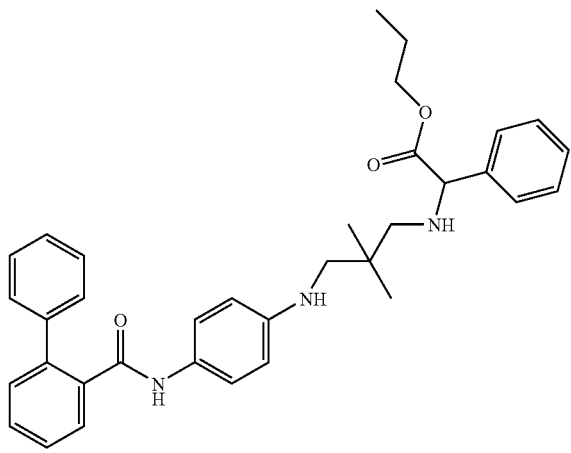
Co. No. 53; Ex. B.2
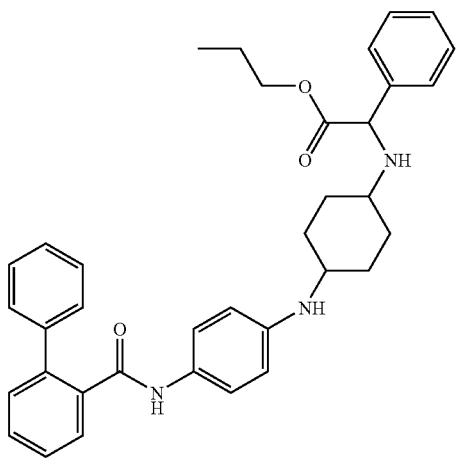
(TRANS); Co. No. 54; Ex. B.2

TABLE F-1-continued
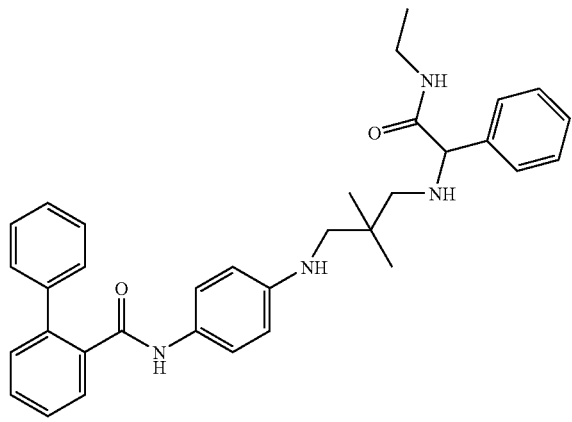
Co. No. 55; Ex. B.2
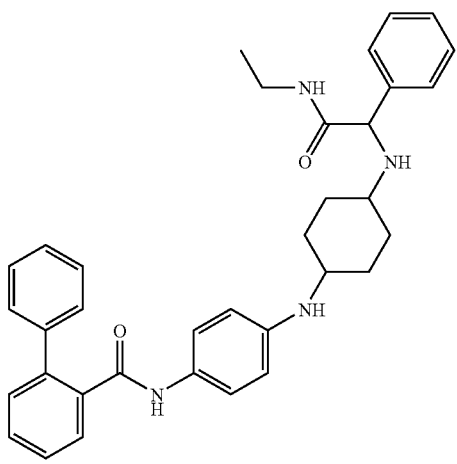
(TRANS); Co. No. 56; Ex. B.2
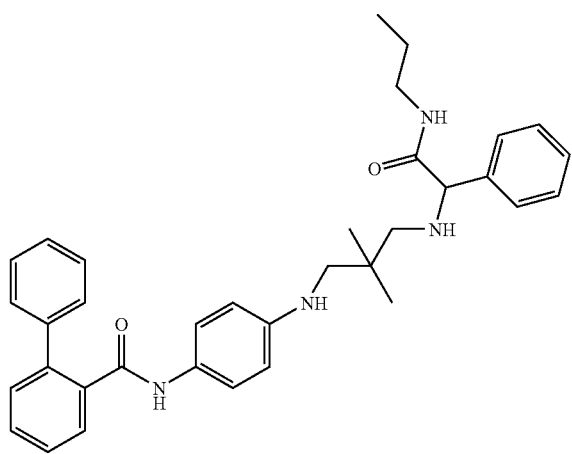
Co. No. 57; Ex. B.2

TABLE F-1-continued
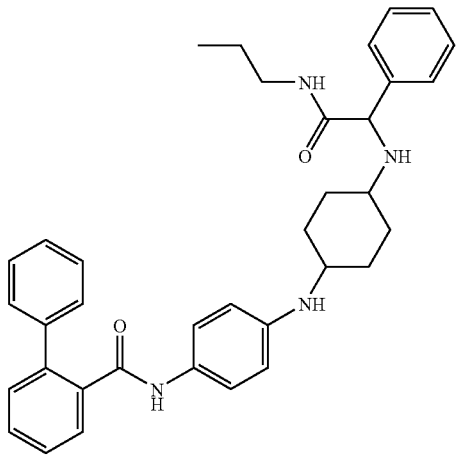
(TRANS); Co. No. 58; Ex. B.2
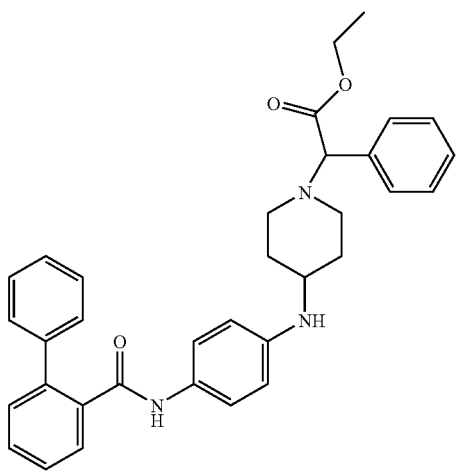
Co. No. 59; Ex. B.3
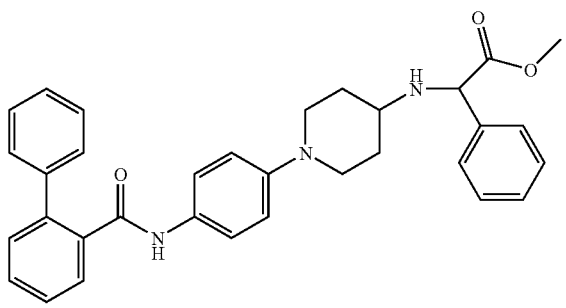
Co. No. 60; Ex. B.3

TABLE F-1-continued
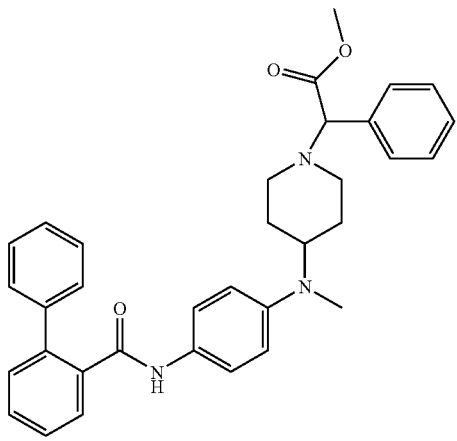
Co. No. 61; Ex. B.3
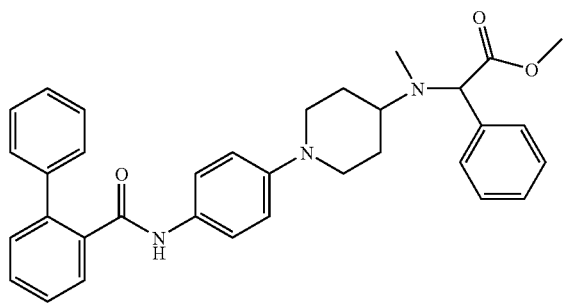
Co. No. 62; Ex. B.3
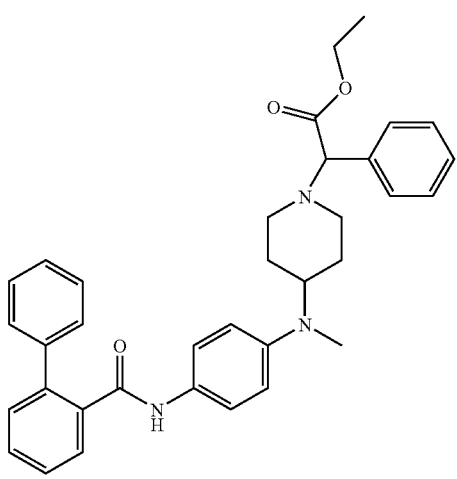
Co. No. 63; Ex. B.3

TABLE F-1-continued
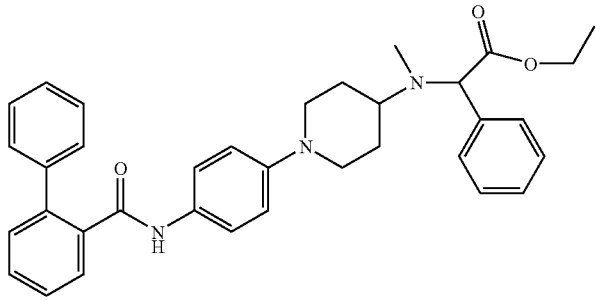
Co. No. 64; Ex. B.3
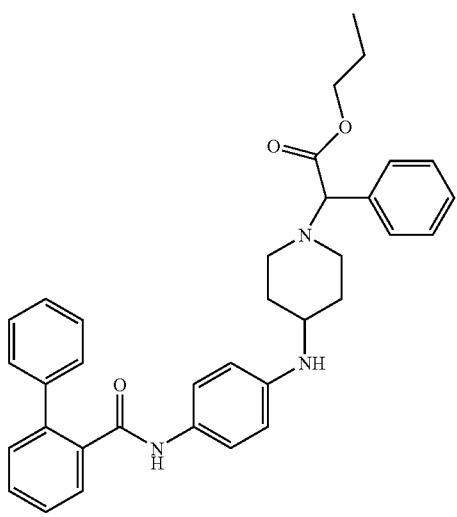
Co. No. 65; Ex. B.3
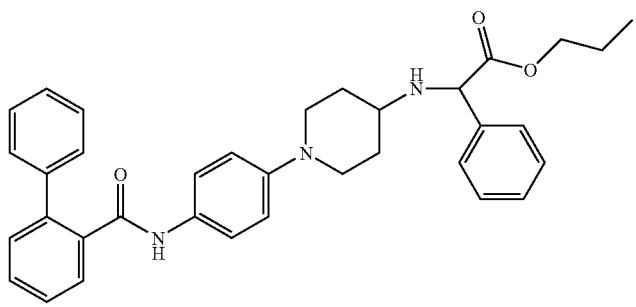
Co. No. 66; Ex. B.3

TABLE F-1-continued
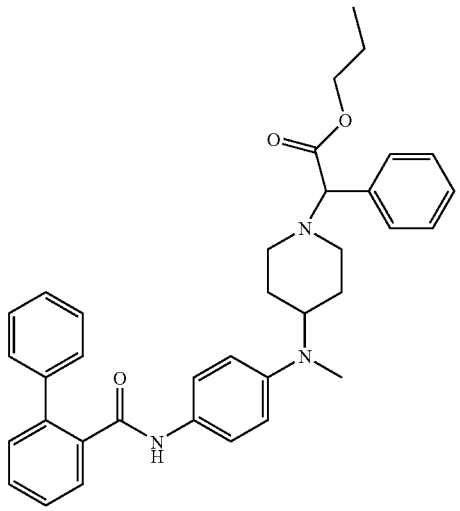
Co. No. 67; Ex. B.3
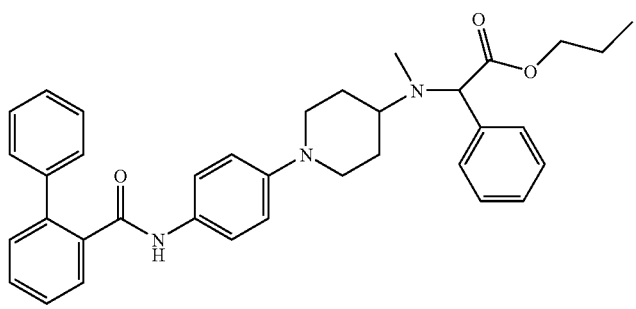
Co. No. 68; Ex. B.3
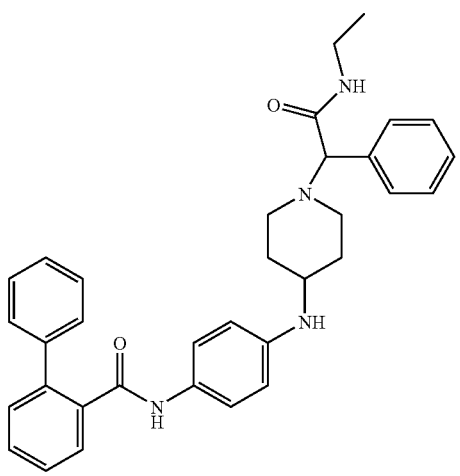
Co. No. 69; Ex. B.3

TABLE F-1-continued
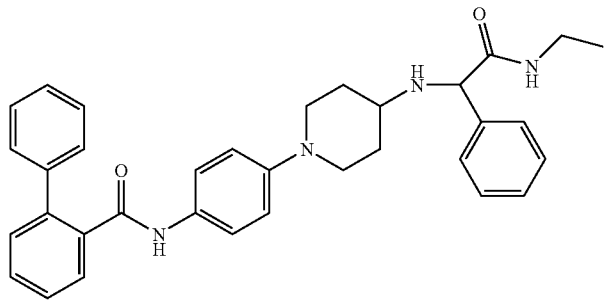
Co. No. 70; Ex. B.3
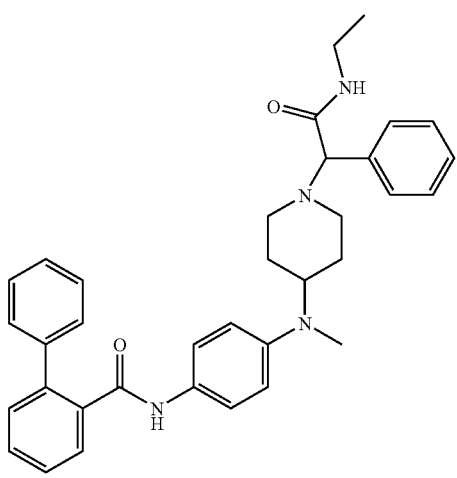
Co. No. 71; Ex. B.3
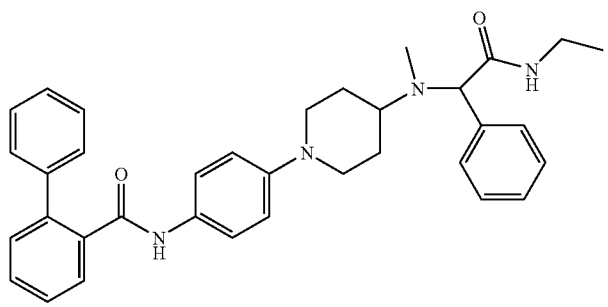
Co. No. 72; Ex. B.3

TABLE F-1-continued
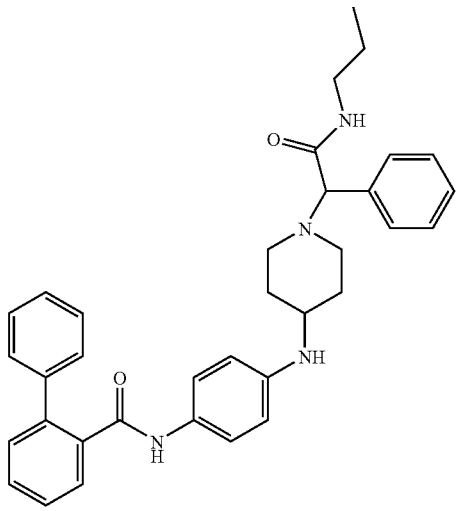
Co. No. 73; Ex. B.3
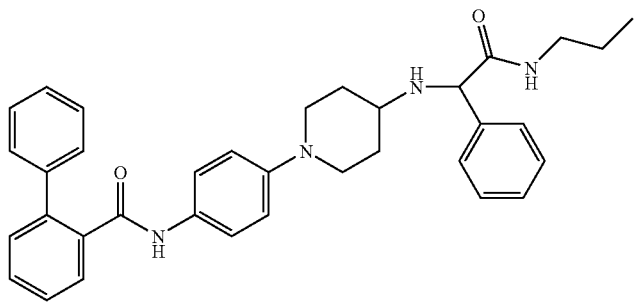
Co. No. 74; Ex. B.3
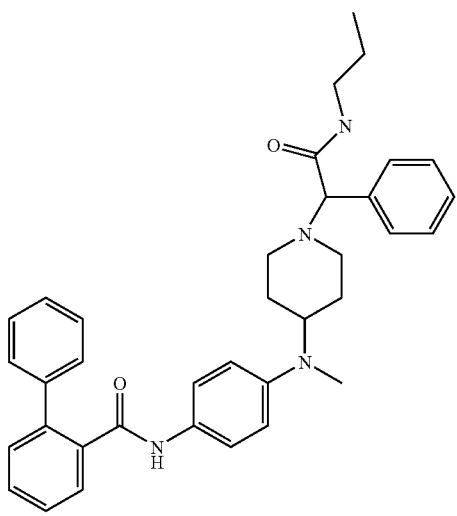
Co. No. 75; Ex. B.3

TABLE F-1-continued
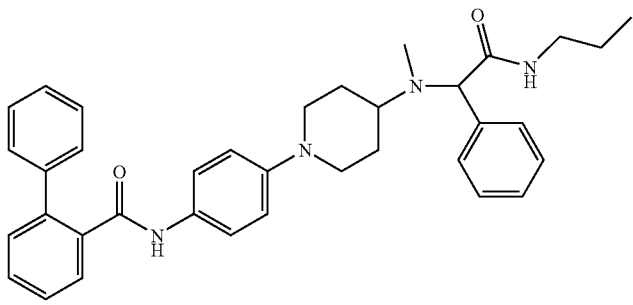
Co. No. 76; Ex. B.3
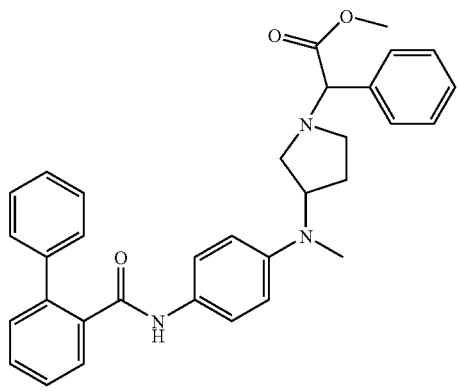
Co. No. 77; Ex. B.3
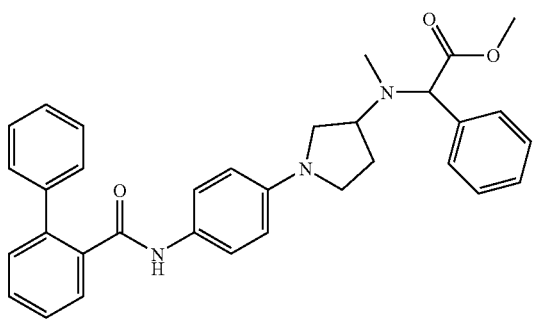
Co. No. 78; Ex. B.3
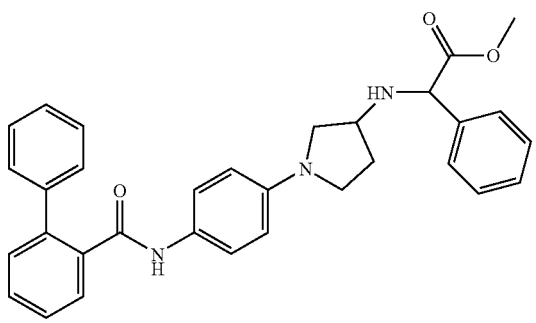
Co. No. 79; Ex. B.3

TABLE F-1-continued
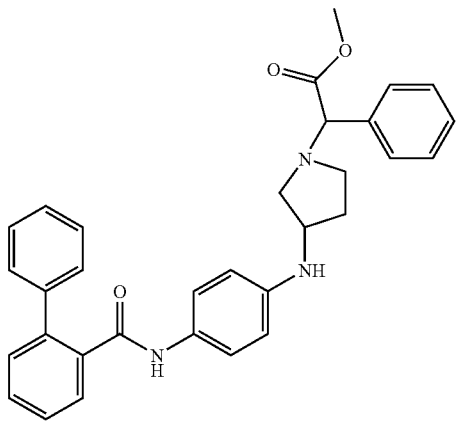
Co. No. 80; Ex. B.3
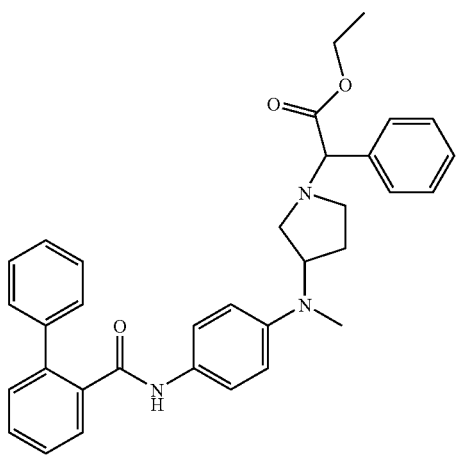
Co. No. 81; Ex. B.3
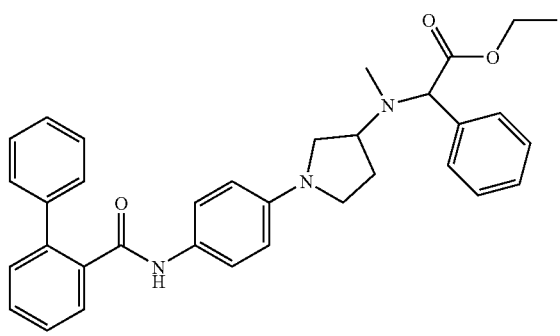
Co. No. 82; Ex. B.3

TABLE F-1-continued
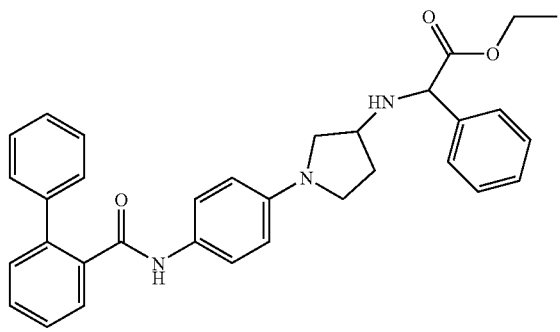
Co. No. 83; Ex. B.3
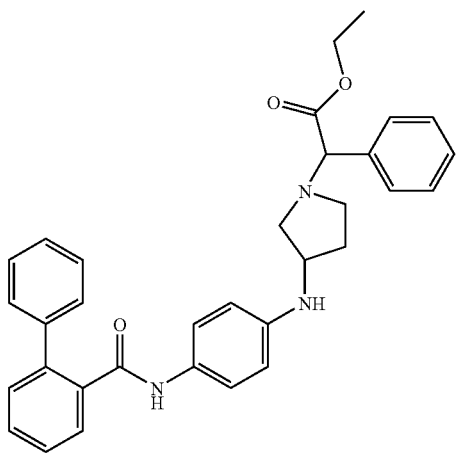
Co. No. 84; Ex. B.3
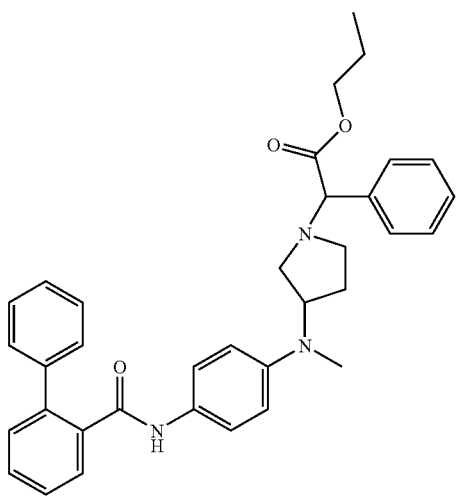
Co. No. 85; Ex. B.3

TABLE F-1-continued
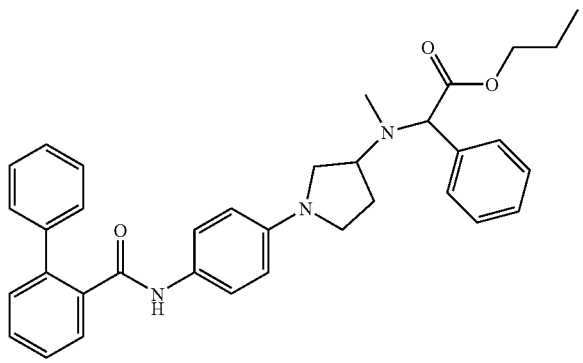
Co. No. 86; Ex. B.3
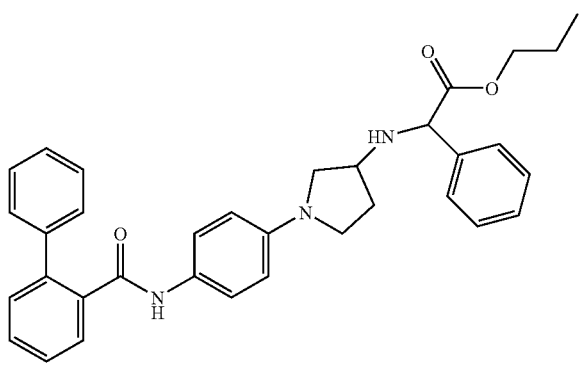
Co. No. 87; Ex. B.3
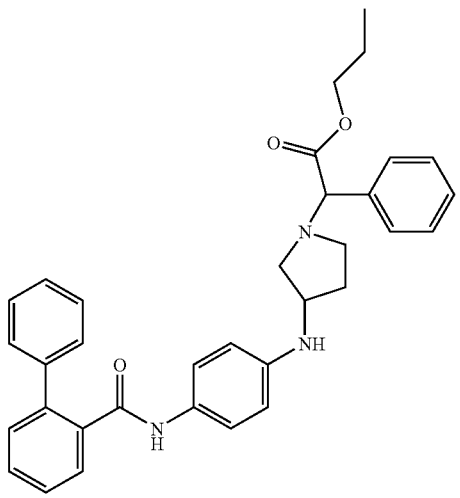
Co. No. 88; Ex. B.3

TABLE F-1-continued
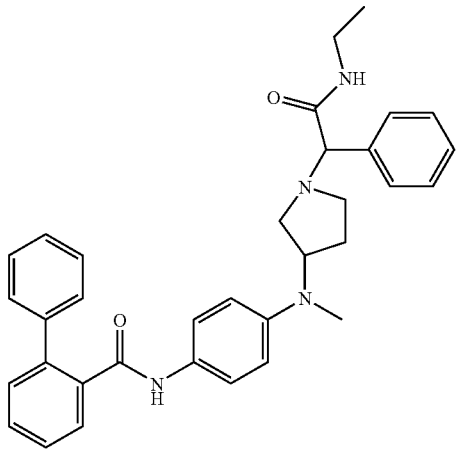
Co. No. 89; Ex. B.3
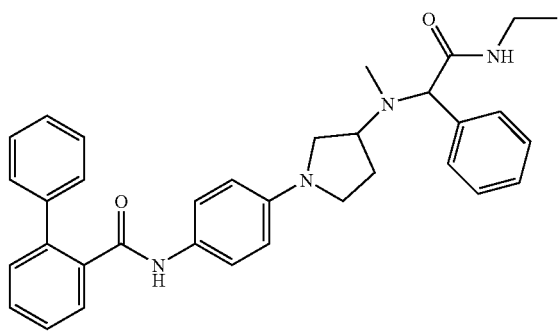
Co. No. 90; Ex. B.3
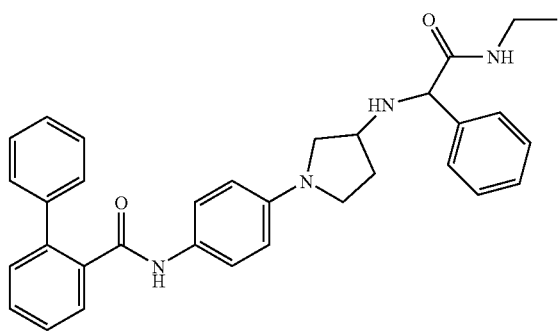
Co. No. 91; Ex. B.3

TABLE F-1-continued
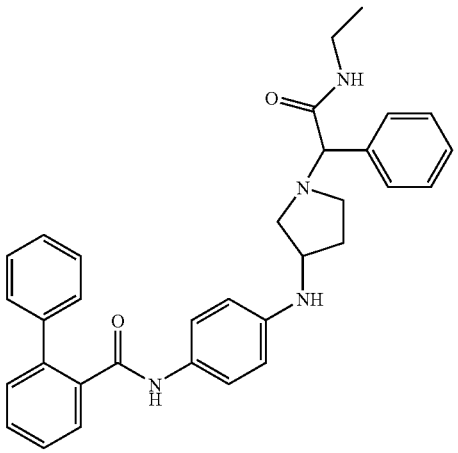
Co. No. 92; Ex. B.3
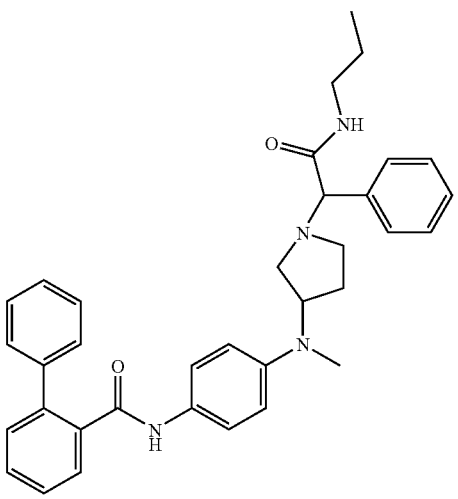
Co. No. 93; Ex. B.3
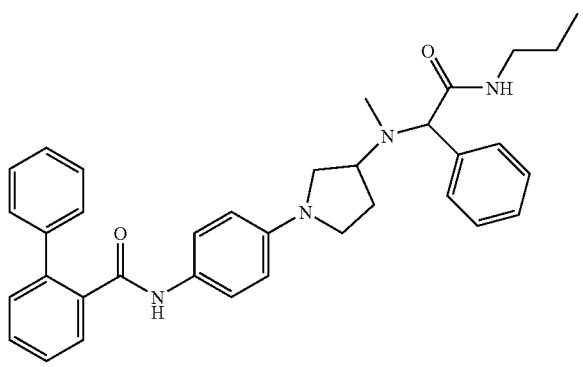
Co. No. 94; Ex. B.3

TABLE F-1-continued
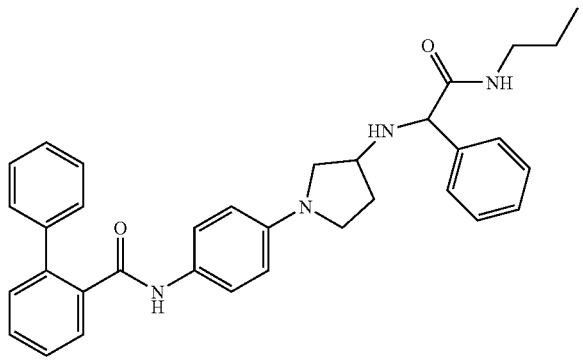
Co. No. 95; Ex. B.3
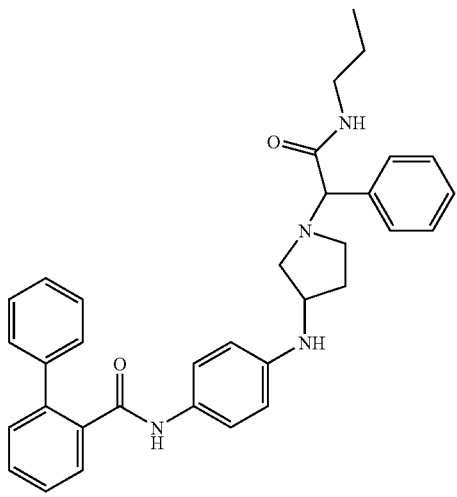
Co. No. 96; Ex. B.3
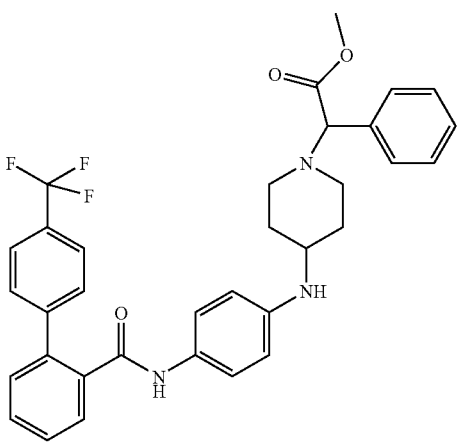
Co. No. 97; Ex. B.4

TABLE F-1-continued
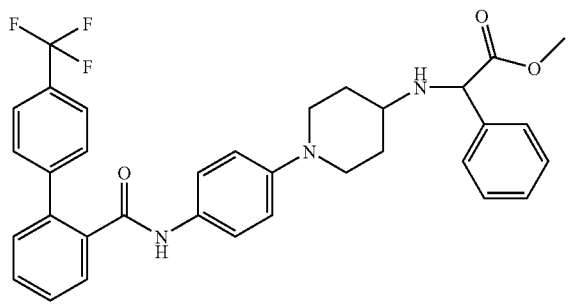
Co. No. 98; Ex. B.4
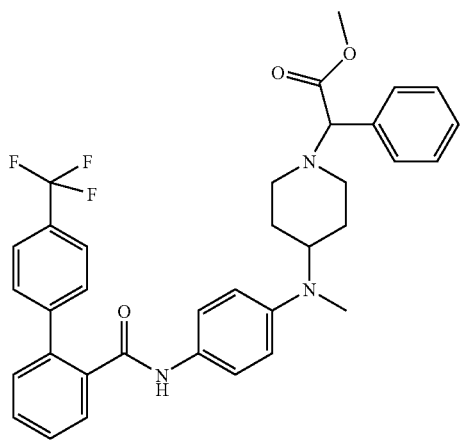
Co. No. 99; Ex. B.4
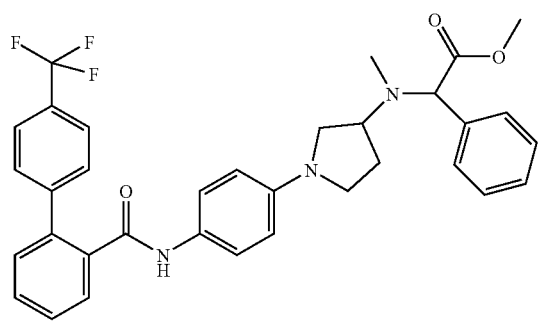
Co. No. 100; Ex. B.4
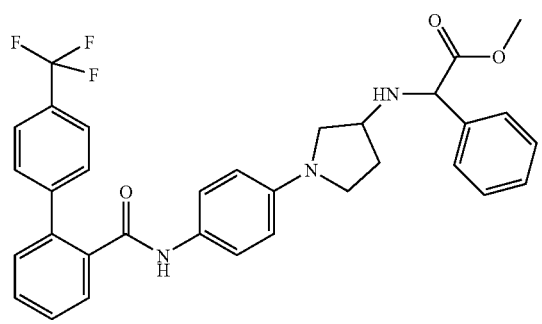
Co. No. 101; Ex. B.4

TABLE F-1-continued
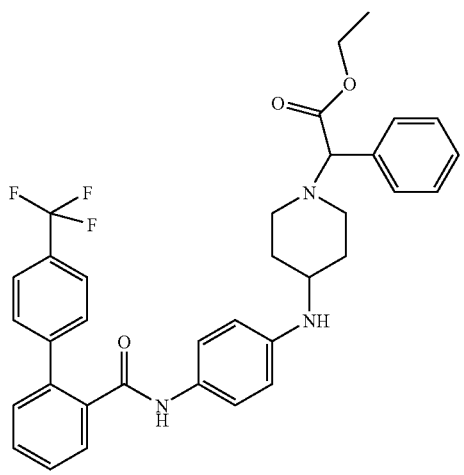
Co. No. 102; Ex. B.4
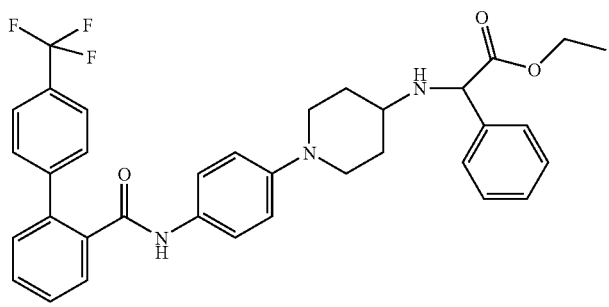
Co. No. 103; Ex. B.4
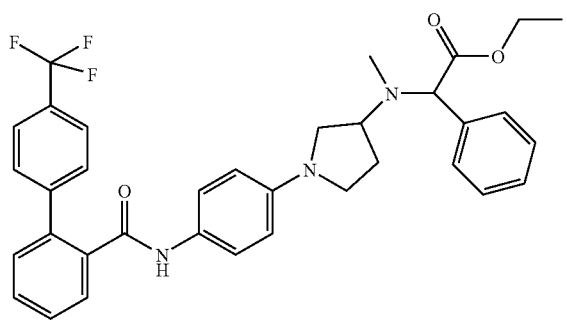
Co. No. 104; Ex. B.4
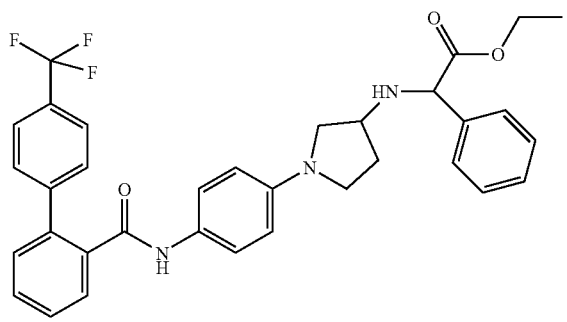
Co. No. 105; Ex. B.4

TABLE F-1-continued
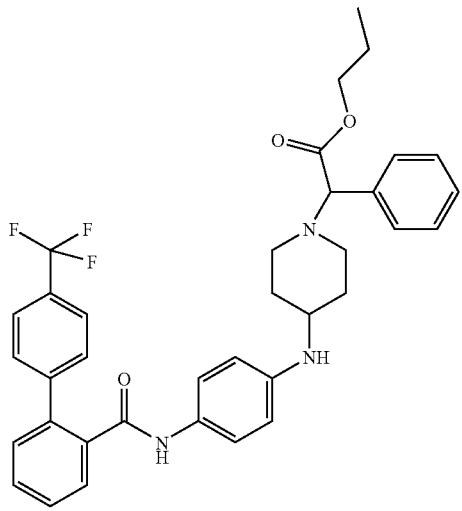
Co. No. 106; Ex. B.4
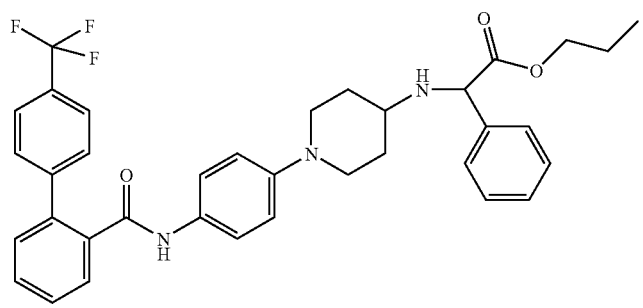
Co. No. 107; Ex. B.4
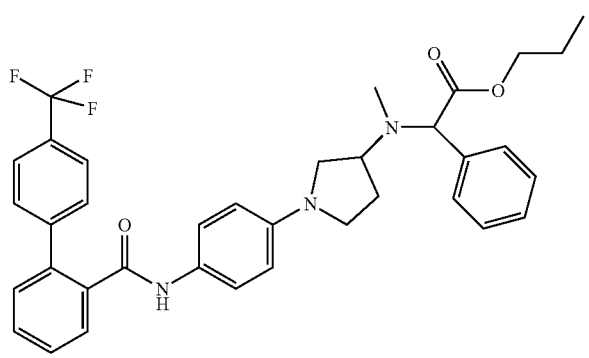
Co. No. 108; Ex. B.4

TABLE F-1-continued
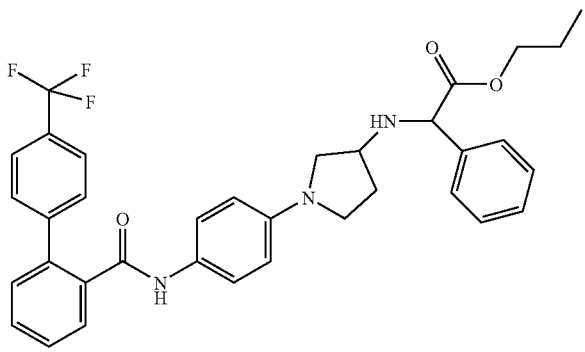
Co. No. 109; Ex. B.4
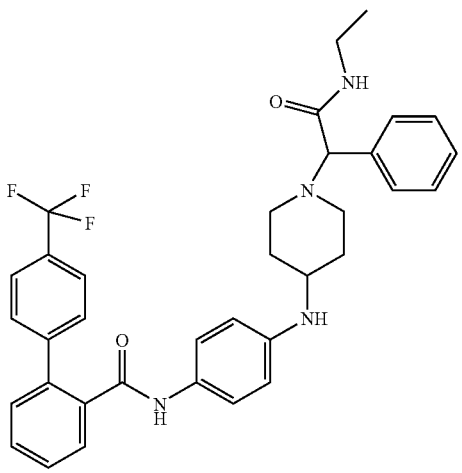
Co. No. 110; Ex. B.4
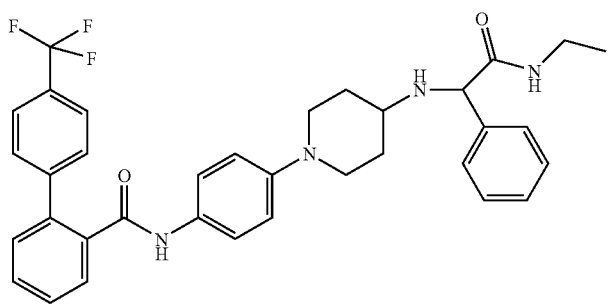
Co. No. 111; Ex. B.4
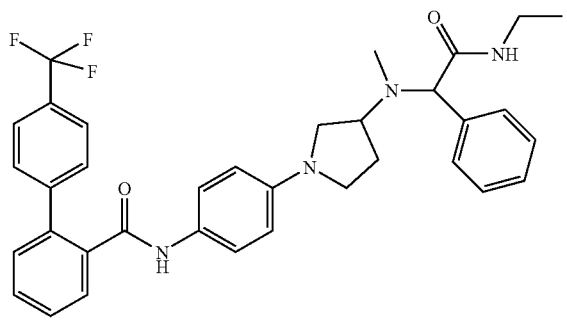
Co. No. 112; Ex. B.4

TABLE F-1-continued
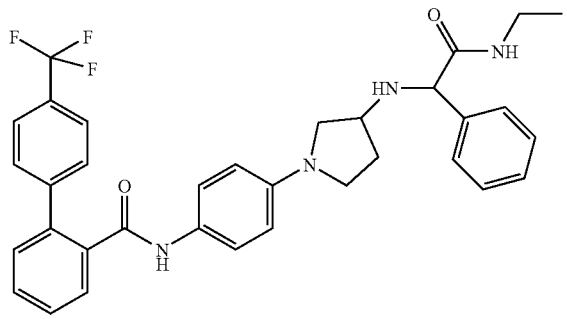
Co. No. 113; Ex. B.4
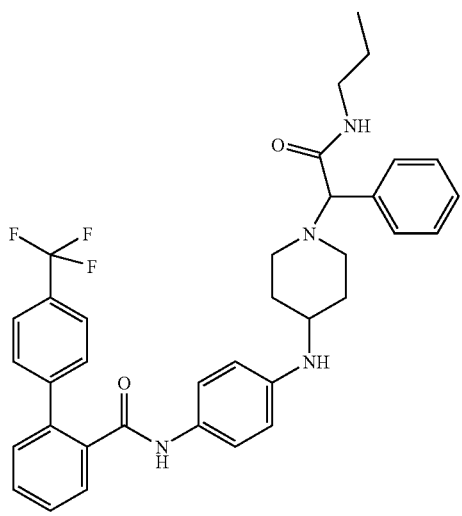
Co. No. 114; Ex. B.4
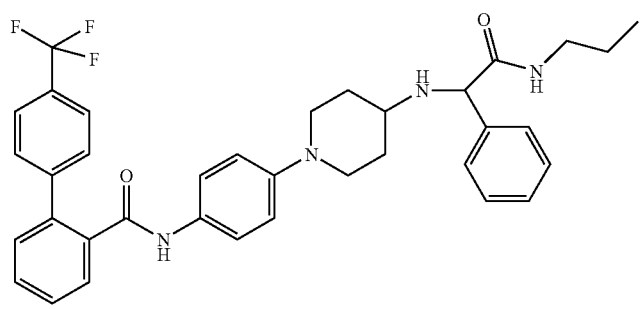
Co. No. 115; Ex. B.4

TABLE F-1-continued
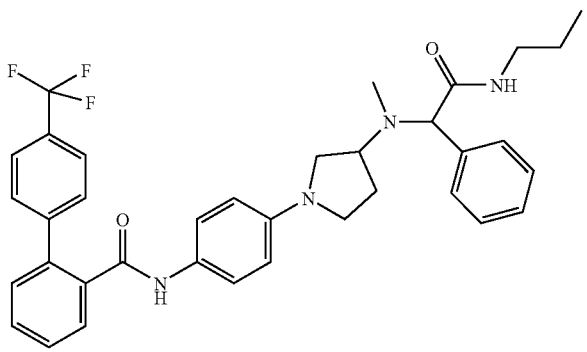
Co. No. 116; Ex. B.4
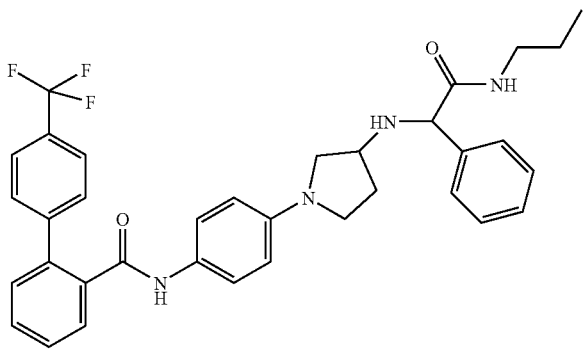
Co. No. 117; Ex. B.4
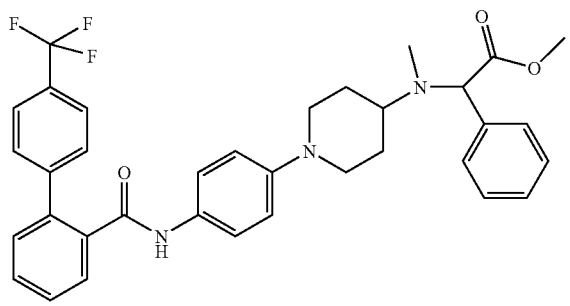
Co. No. 118; Ex. B.4
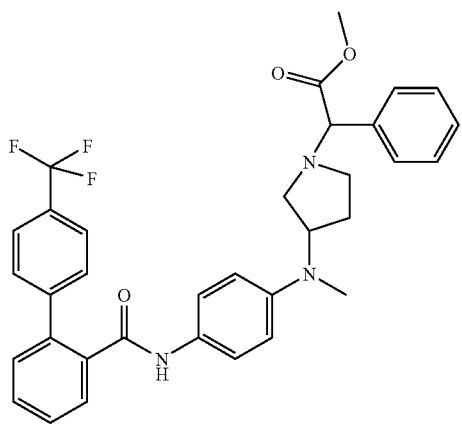
Co. No. 119; Ex. B.4

TABLE F-1-continued
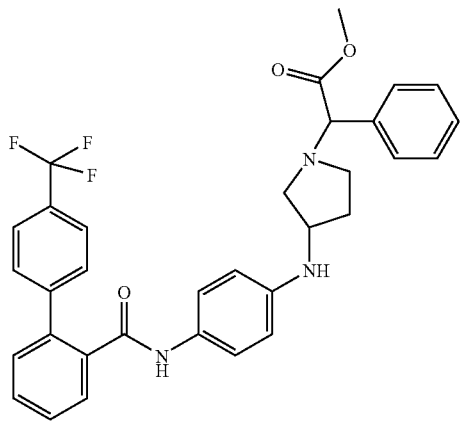
Co. No. 120; Ex. B.4
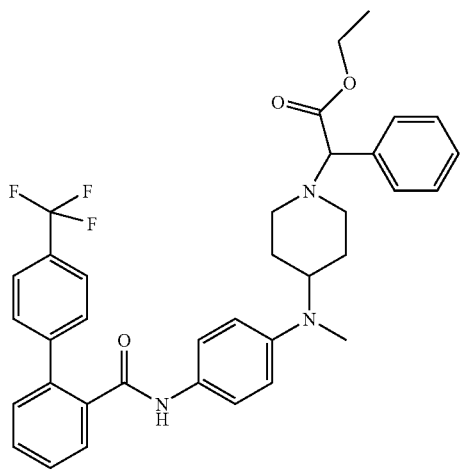
Co. No. 121; Ex. B.4
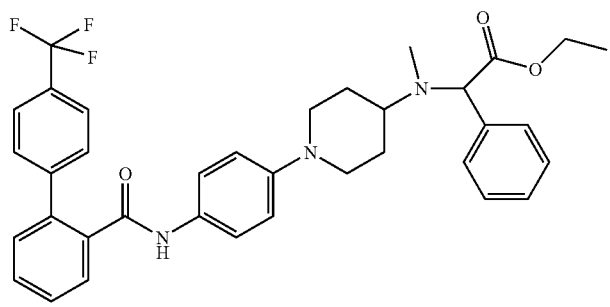
Co. No. 122; Ex. B.4

TABLE F-1-continued
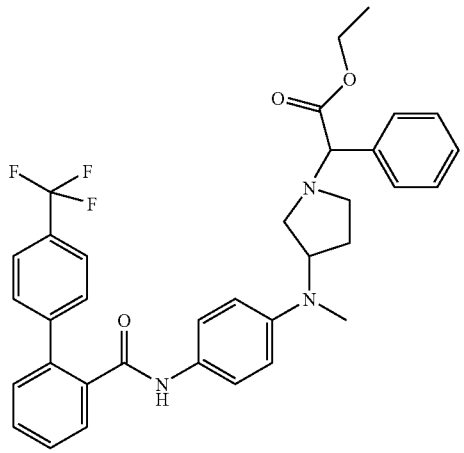
Co. No. 123; Ex. B.4
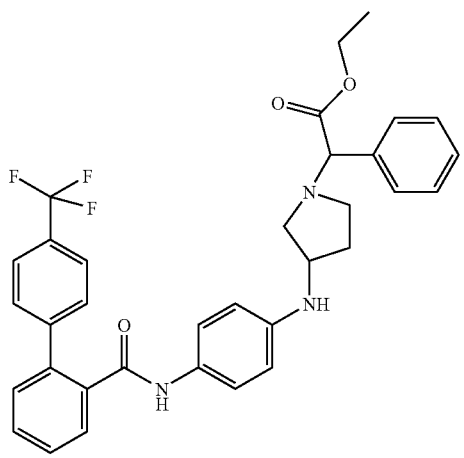
Co. No. 124; Ex. B.4
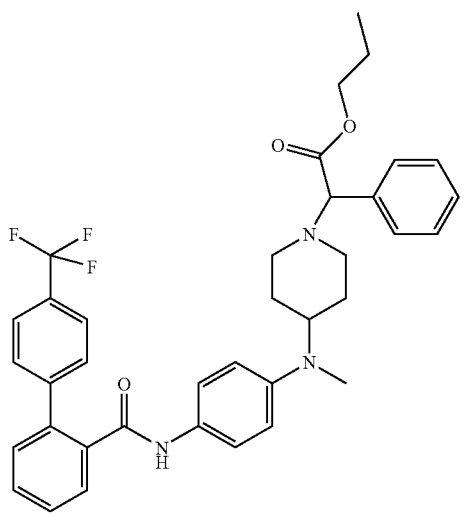
Co. No. 125; Ex. B.4

TABLE F-1-continued
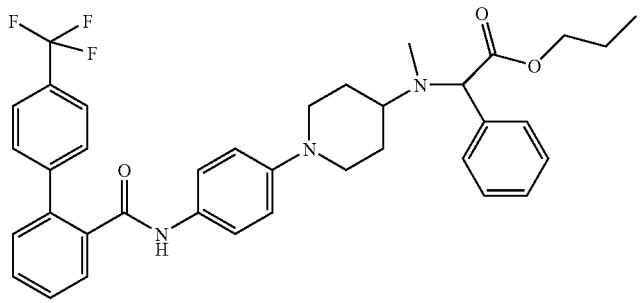
Co. No. 126; Ex. B.4
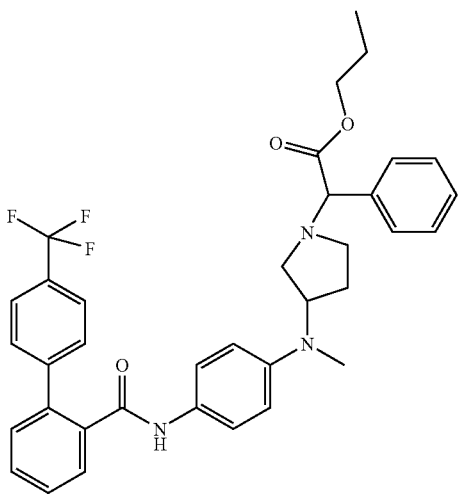
Co. No. 127; Ex. B.4
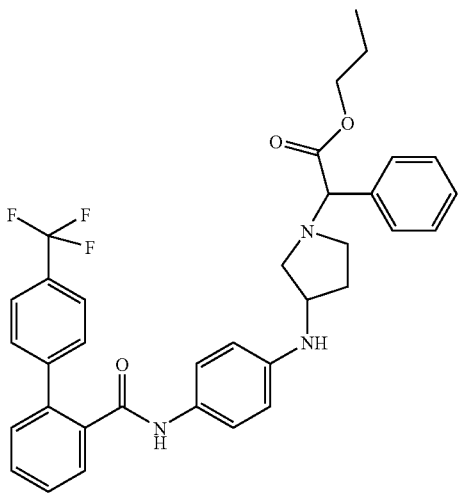
Co. No. 128; Ex. B.4

TABLE F-1-continued
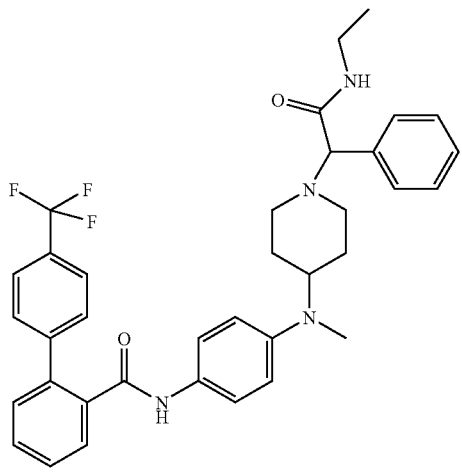
Co. No. 129; Ex. B.4
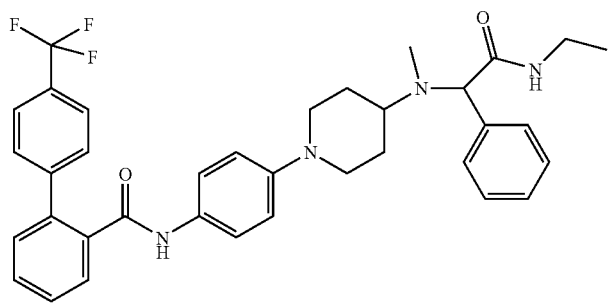
Co. No. 130; Ex. B.4
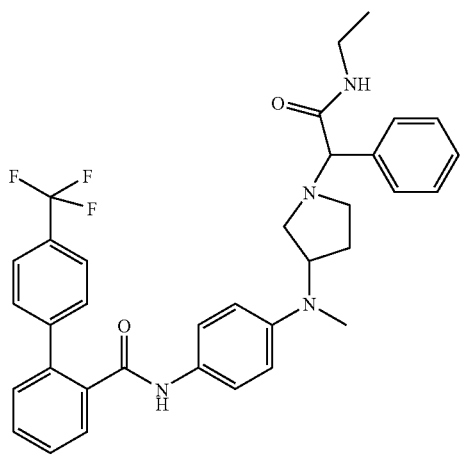
Co. No. 131; Ex. B.4

TABLE F-1-continued
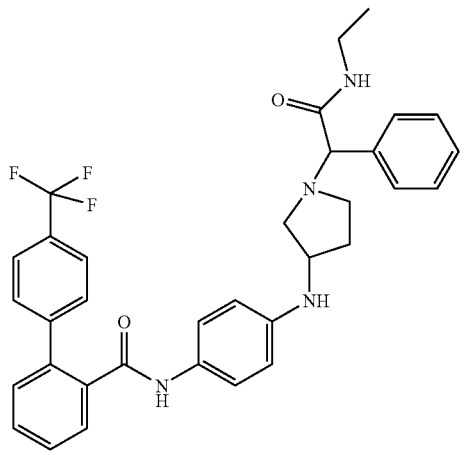
Co. No. 132; Ex. B.4
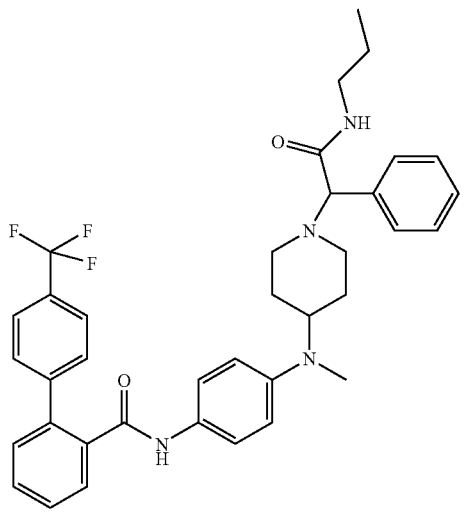
Co. No. 133; Ex. B.4
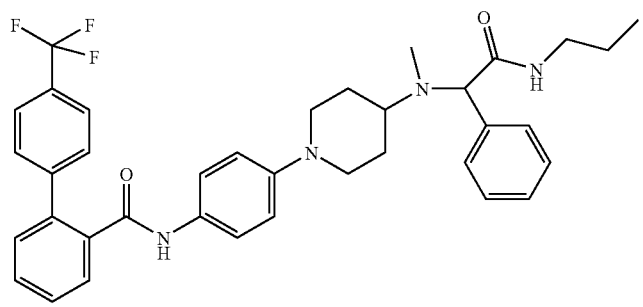
Co. No. 134; Ex. B.4

TABLE F-1-continued

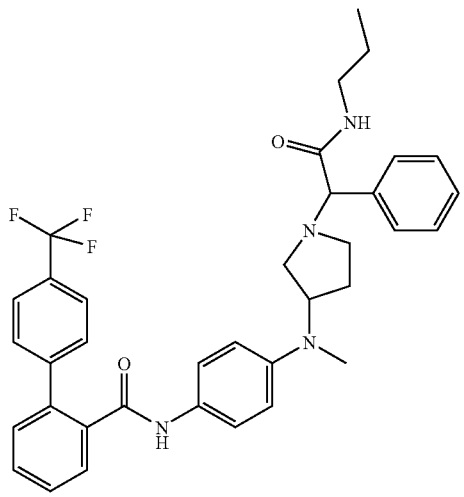

Co. No. 135; Ex. B.4

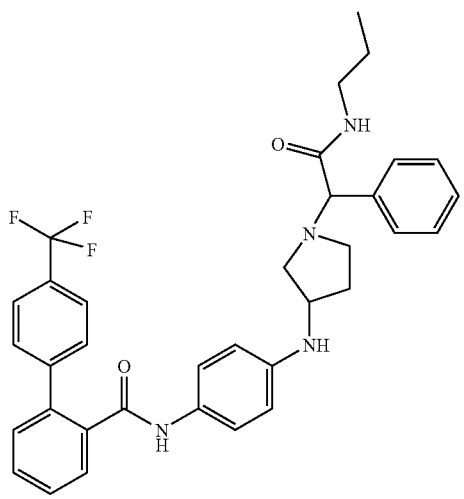

Co. No. 136; Ex. B.4

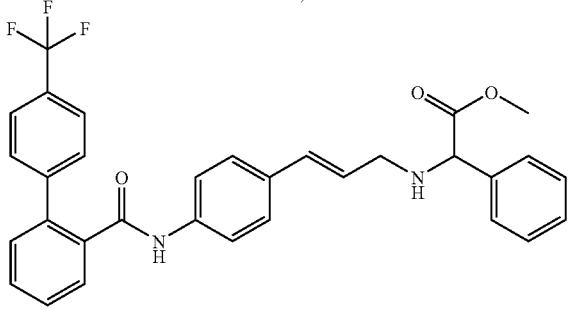

Co. No. 137; Ex. B.5

C. PHARMACOLOGICAL EXAMPLES.

C.1. Quantification of the Secretion of ApoB.

HepG2 cells were cultured in 24-well plates in MEM Rega 3 containing 10% fetal calf serum. At 70% confluency, the medium was changed and the test compound or carrier (DMSO, 0.4% final concentration) was added. After 24 hours of incubation, the medium was transferred to Eppendorf tubes and cleared by centrifugation. A sheep antibody directed against either apoB was added to the supernatant and the mixture was kept at 8° C. for hours. Then, rabbit anti-sheep antibody was added and the immune complex was allowed to precipitate for 24 hours at 8° C. The immunoprecipitate was pelleted by centrifugation for 25 minutes at 1320 g and washed twice with a buffer containing 40 mM Mops, 40 mM NaH$_2$PO$_4$, 100 mM NaF, 0.2 mM DTT, 5 mM EDTA, 5 mM EGTA, 1% Triton-X-100, 0.5% sodium deoxyxholate (DOC), 0.1% SDS, 0.2 µM leupeptin and 0.2 µM PMSF. Radioactivity in the pellet was quantified by liquid scintillation counting.

Resulting IC$_{50}$ values are enumerated in Table C.1.

TABLE C.1 pIC50 values (= -log IC$_{50}$ value)

| Compound number | pIC50 |
|---|---|
| 1 | 7.149 |
| 2 | 6.499 |
| 3 | 6.116 |
| 4 | 7.007 |
| 5 | 5.992 |
| 6 | 5.683 |
| 7 | 6.482 |
| 8 | 6.888 |
| 9 | 6.247 |
| 10 | 6.023 |
| 11 | 5.862 |
| 12 | 6.162 |
| 13 | 6.312 |
| 14 | 6.028 |
| 15 | 6.121 |
| 16 | 5.899 |
| 17 | 6.092 |
| 18 | >7.523 |
| 19 | 6.641 |
| 20 | 5.715 |
| 21 | 6.296 |
| 22 | 5.987 |
| 23 | 5.805 |
| 24 | 6.766 |
| 25 | 6.023 |
| 26 | 5.706 |
| 27 | 6.204 |
| 28 | 5.826 |
| 29 | 6.123 |
| 98 | 5.801 |
| 100 | 7.38 |
| 101 | 7.388 |
| 102 | <5.523 |
| 103 | 5.796 |
| 104 | >7.523 |
| 105 | 6.737 |
| 106 | 5.523 |
| 107 | 5.805 |
| 108 | 7.161 |
| 109 | 6.823 |
| 110 | 5.93 |
| 111 | 6.458 |
| 112 | 7.404 |
| 113 | 7.97 |
| 114 | 5.583 |
| 115 | 6.023 |
| 116 | 7.023 |
| 117 | >7.523 |

C.2. MTP Assay

MTP activity was measured using an assay similar to one described by J. R. Wetterau and D. B. Zilversmit in *Chemistry and Physics of Lipids*, 38, 205–222 (1985). To prepare the donor and acceptor vesicles, the appropriate lipids in chloroform were put into a glass test tube and dried under a stream of N$_2$. A buffer containing 15 mM Tris-HCl pH 7.5, 1 mM EDTA, 40 mM NaCl, 0.02% NaN$_3$ (assay buffer) was added to the dried lipid. The mixture was vortexed briefly and the lipids were then allowed to hydrate for 20 min on ice. Vesicles were then prepared by bath sonication (Branson 2200) at room temperature for maximum 15 min. Butylated hydroxytoluene was included in all vesicle preparations at a concentration of 0.1%. The lipid transfer assay mixture contained donor vesicles (40 mmol phosphatidylcholine, 7.5 mol % of cardiolipin and 0.25 mol % glycerol tri [1-$^{14}$C]-oleate), acceptor vesicles (240 nmol phosphatidylcholine) and 5 mg BSA in a total volume of 675 µl in a 1.5 ml microcentrifuge tube. Test compounds were added dissolved in DMSO (0.13% final concentration). After 5 minutes of pre-incubation at 37° C., the reaction was started by the addition of MTP in 100 µl dialysis buffer. The reaction was stopped by the addition of 400 µl DEAE-52 cellulose pre-equilibrated in 15 mM Tris-HCl pH 7.5, 1 mM EDTA, 0.02% NaN$_3$ (1:1, vol/vol). The mixture was agitated for 4 min and centrifuged for 2 min at maximum speed in an Eppendorf centrifuge (4° C.) to pellet the DEAE-52-bound donor vesicles. An aliquot of the supernatant containing the acceptor liposomes was counted and the [$^{14}$C]-counts were used to calculate the percent triglyceride transfer from donor to acceptor vesicles.

The invention claimed is:

1. A compound of formula (I)

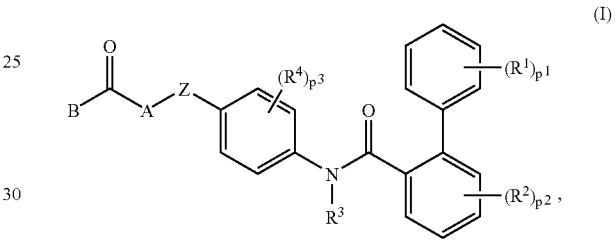

the N-oxides, the pharmaceutically acceptable acid addition salts and the stereochemically isomeric forms thereof, wherein $p^1$, $p^2$ and $p^3$ are integers each independently from 1 to 3;

each $R^1$ is independently selected from hydrogen, $C_{1-4}$alkyl, $C_{1-4}$alkyloxy, halo, hydroxy, mercapto, cyano, nitro, $C_{1-4}$alkylthio or polyhalo$C_{1-6}$alkyl, amino, $C_{1-4}$alkylamino and di($C_{1-4}$alkyl)amino;

each $R^2$ is independently selected from hydrogen, $C_{1-4}$alkyl, $C_{1-4}$alkyloxy, halo, or trifluoromethyl;

$R^3$ is hydrogen of $C_{1-4}$alkyl;

each $R^4$ is independently selected from hydrogen $C_{1-4}$alkyl, $C_{1-4}$alkyloxy, halo, or trifluoromethyl;

Z is a bivalent radical of formula

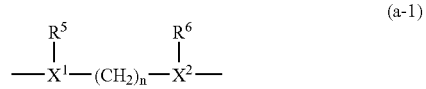

wherein n is an integer from 2 to 4 and the —(CH$_2$)$_n$— moiety in radical (a-1) may optionally be substituted with one or two $C_{1-4}$alkyl;

$R^5$ and $R^6$ are each independently selected from hydrogen, $C_{1-6}$alkyl or aryl;

$X^1$ and $X^2$ are each N;

A represents a bond, $C_{1-6}$alkanediyl optionally substituted with one or two groups selected from aryl, and $C_{3-10}$cycloalkyl;

B represents hydrogen; $C_{1-10}$alkyl; or aryl each optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkoxycarbonyl, $C_{1-10}$alkylaminocarbonyl and di($C_{1-10}$alkyl)aminocarbonyl; aryl$C_{1-10}$alkyl; $C_{3-10}$cycloalkyl; polyhalo$C_{1-6}$alkyl; $C_{3-6}$alkenyl; $C_{3-6}$alkynyl; $NR^7R^8$; or $OR^9$;

wherein $R^7$ and $R^8$ each independently represent hydrogen, $C_{1-10}$alkyl, or aryl each optionally substituted with a group selected from halo, cyano, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkylaminocarbonyl and di($C_{1-10}$alkyl)aminocarbonyl; aryl$C_{1-10}$alkyl, $C_{3-10}$cycloalkyl, $C_{7-10}$polycycloalkyl, polyhalo$C_{1-6}$alkyl, $C_{3-8}$alkenyl, $C_{3-8}$alkynyl, fused benzo-$C_{5-8}$cycloalkyl, and wherein $R^9$ represents $C_{1-10}$alkyl, or aryl each optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkylaminocarbonyl and di($C_{1-10}$alkyl)aminocarbonyl; aryl$C_{1-10}$alkyl; $C_{3-10}$cycloalkyl; $C_{7-10}$polycycloalkyl; polyhalo$C_{1-6}$alkyl; $C_{3-8}$alkenyl; $C_{3-8}$alkynyl; or fused benzo$C_{5-8}$cycloalkyl.

2. A compound as claimed in claim 1 wherein $R^1$ is hydrogen or trifluoromethyl; $R^2$, $R^3$ and $R^4$ are hydrogen; and Z is a bivalent radical of formula (a-1) wherein $X^1$ and $X^2$ are each nitrogen, n is the integer 2, and $R^5$ and $R^6$ are each independently hydrogen or methyl.

3. A compound as claimed in any of claim 1 to wherein A is $C_{1-6}$alkanediyl substituted with phenyl and B is $C_{1-4}$alkyloxy, or $C_{1-10}$alkylamino.

4. A pharmaceutical composition comprising a pharmaceutically acceptable carrier and a therapeutically active amount of a compound as claimed in claim 1.

5. A process for preparing a compound of formula (I) wherein a) an intermediate of formula (II), wherein B, A, Z, $R^4$ and $p^3$ are defined as in claim 1,

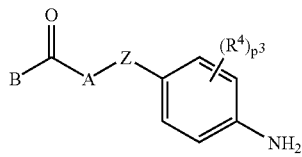

(II)

is reacted with a biphenylcarboxylic acid or halide having the formula (III), wherein $R^1$, $R^2$, $p^1$ and $p^2$ are as defined in formula (I) and $Y^1$ is selected from hydroxy and halo, in at least one reaction-inert solvent and optionally in the presence of a suitable base

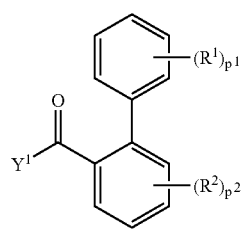

(III)

b) an intermediate having the formula (IV)

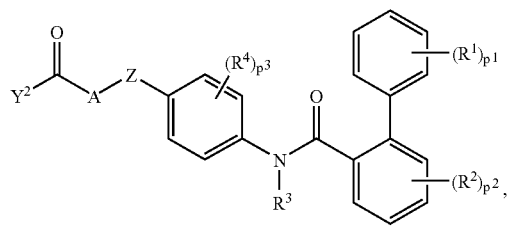

(IV)

wherein $R^1$, $R^2$, $R^3$, $R^4$, A, Z, $p^1$, $p^2$ and $p^3$ are defined as in claim 1 and $Y^2$ is selected from halo and hydroxy, is reacted with an intermediate (V) of the formula B-H, wherein B is $NR^7R^8$ or $OR^9$ and $R^7$, $R^8$ and $R^9$ are defined as in claim 1, in at least one reaction-inert solvent and optionally in the presence of at least one suitable coupling reagent and/or a suitable base;

c) an intermediate of formula (VI), wherein $R^1$, $R^2$, $R^3$, $R^4$, $p^1$, $p^2$ and $p^3$ are defined as in claim 1 and $Y^3$ is selected from halo, $B(OH)_2$, alkylboronates and cyclic analogues thereof,

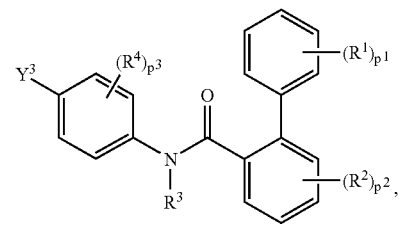

(VI)

is reacted with a reactant having the formula (VII), wherein B, A and Z are defined as in claim 1, in at least one reaction-inert solvent and optionally in the presence of at least one transition metal coupling reagent and/or at least one suitable ligand;

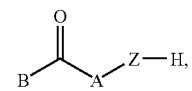

(VII)

d) or, compounds of formula (I) are converted into each other following art-known transformation reactions; or if desired; a compound of formula (I) is converted into an acid addition salt, or conversely, an acid addition salt of a compound of formula (I) is converted into a free base form with alkali; and, if desired, preparing stereochemically isomeric forms thereof.

* * * * *